(12) United States Patent
Trifunov

(10) Patent No.: US 8,719,051 B2
(45) Date of Patent: May 6, 2014

(54) SYSTEM AND METHOD FOR EVALUATING AND COMPARING MEDICAL TREATMENTS

(75) Inventor: Patricia Trifunov, Wynnewood, PA (US)

(73) Assignee: Gear Five Health Solutions, Inc., Wynnewood, PA (US)

( * ) Notice: Subject to any disclaimer, the term of this patent is extended or adjusted under 35 U.S.C. 154(b) by 184 days.

(21) Appl. No.: 13/286,184

(22) Filed: Oct. 31, 2011

(65) Prior Publication Data
US 2012/0185266 A1    Jul. 19, 2012

Related U.S. Application Data

(60) Provisional application No. 61/432,518, filed on Jan. 13, 2011.

(51) Int. Cl.
*G06Q 50/22* (2012.01)
*G06Q 50/24* (2012.01)

(52) U.S. Cl.
CPC ............... *G06Q 50/22* (2013.01); *G06Q 50/24* (2013.01)
USPC .................................................. 705/2; 705/3

(58) Field of Classification Search
CPC ............................. G06Q 50/22; G06Q 50/24
USPC .................................................... 705/2–3
See application file for complete search history.

(56) References Cited

U.S. PATENT DOCUMENTS

| | | | |
|---|---|---|---|
| 6,081,786 A * | 6/2000 | Barry et al. | 705/3 |
| 8,224,665 B2 * | 7/2012 | Morris | 705/2 |
| 2005/0228692 A1 * | 10/2005 | Hodgdon | 705/2 |
| 2005/0234742 A1 * | 10/2005 | Hodgdon | 705/2 |
| 2009/0326976 A1 * | 12/2009 | Morris | 705/2 |
| 2011/0106556 A1 * | 5/2011 | Patel et al. | 705/2 |
| 2012/0179480 A1 * | 7/2012 | Patel et al. | 705/2 |
| 2012/0245953 A1 * | 9/2012 | Morris | 705/2 |

* cited by examiner

*Primary Examiner* — Eliza Lam
(74) *Attorney, Agent, or Firm* — CipherLaw

(57) ABSTRACT

An evaluative software tool to support the assessment of health care-related technologies during development to facilitate making critical decisions for an optimized research, development and commercialization plan is provided. The software tool includes the ability to measure, weight, and integrate the critical factors that come into play in the development of a risk/benefit profile of a technology relative to its competitors, benchmarked around clinical trial measures, in order to determine its development and commercialization success.

20 Claims, 32 Drawing Sheets

Velocity BioGroup Advanced Modeling System

Home  Model Scalings  Reports  Config  My Profile

Jump to Screen: -- Select Screen --   (Save)

« Prev                                                                Next »

VALUE PROPOSITION - MEASURE SCALINGS
*Enter numeric values corresponding to the relative weightings among items.*

| | | |
|---:|:---:|---:|
| Cost Effectiveness vs. Treatment as Usual: | 6 | 31.58% |
| Relative to ICER Budgetary Boundaries: | 3 | 15.79% |
| Arrests and Re-Incarceration Rates: | 3 | 15.79% |
| Physician/Clinic Use: | 1 | 5.26% |
| Short Form 36 or ED-SD Quality of Life: | 1 | 5.26% |
| Beck or Montgomery Asberg Depression Rating: | 1 | 5.26% |
| Quality of Life, Enjoyment and Satisfaction Questionnaire (QLESQ): | 1 | 5.26% |
| Addiction Severity Index - Lite Version (ASI-Lite): | 3 | 15.79% |

FIG. 8

Velocity BioGroup Advanced Modeling System

Home   Model   Scalings   Reports   Config   My Profile

Jump to Screen:   -- Select Screen --  ▼          (Save)

« Prev                                                                    Next »

REIMBURSEMENT & ADMINISTRATION - MEASURE SCALINGS

*Enter numeric values corresponding to the relative weightings among items.*

| | | |
|---:|:---:|:---:|
| Ease of Use | 1 | 5.00% |
| Storage Factors | 1 | 5.00% |
| Ease of Administration | 2 | 10.00% |
| Shipping & Distribution Requirements | 0.5 | 2.50% |
| Narcotic Schedule | 0.5 | 2.50% |
| Federal Bureau of Prisons - Alternative Sentencing | 2 | 10.00% |
| Top 10 State Programs - Alternative Sentencing | 4 | 20.00% |
| Top 10 State Programs - Medicaid Expansion | 3 | 15.00% |
| Drug Rehab Centers | 2 | 10.00% |
| Likelihood for Unrestrictive Government Access | 4 | 20.00% |

SYSTEM AND METHOD FOR EVALUATING AND COMPARING MEDICAL TREATMENTS

CROSS REFERENCE TO RELATED APPLICATIONS

The present application is related to and claims priority from prior provisional application Ser. No. 61/432,518 filed by Pat Trifunov on Jan. 13, 2011 and entitled "Medical Assessment and Pricing Tool", the contents which are incorporated herein by reference.

FIELD OF THE INVENTION

The present invention relates to a software tool useful for evaluating and comparing a plurality of different medical treatments.

BACKGROUND

It is estimated that the cost to bring a new drug to market is, on average, about $800 million. However, despite the large investment involved, assessing a medical treatment's potential for development and commercialization success is often elusive. Moreover, the health care industry is noted for having a culture that fosters an inefficient decision making process. As such, various treatments in the last several years have failed to live up to initial expectations.

Although market forecast models are available, they do not have the ability to measure, weight, and integrate the critical factors that come into play in the development of a medical treatment relative to competing treatments. Furthermore, most of the other software tools that exist in the pharmaceutical industry are designed for use in a particular area. For instance, research-related software has been built to specifically address research needs. Likewise, commercial software products respond only to sales and marketing needs.

SUMMARY

In a preferred embodiment of the present invention, the present invention comprises a computer system including non-transitory computer-readable memory that stores one or more code segments (i.e., a computer program) including the software of the invention executable by the computer system. When executed on the computer system, the present invention transforms the computer system into a software tool useful for evaluating and comparing a plurality of different medical treatments.

The present invention can be used for assessing the comparative benefits and risks of a new technology relative to other comparable marketed or emerging technologies. These benefits and risks can be scaled to reflect proportionate value of marketplace and stakeholder feedback, thus capturing the relative importance of the data. By doing so, the tool can be used to predict overall innovation development and commercialization success.

Evaluated technology candidates can be displayed relative to the benefits and risks for success on both a comprehensive scorecard and a four-quadrant risk/benefit graph. The data used in the model can come from many sources: clinical trials, medical literature, electronic medical records, retrospective database analyses, stakeholder feedback and historical commercialization trends or factors, etc. This information may be input to the model using a variety of screens and/or input as an initial set of predetermined values. In many cases, the model allows for scaling adjustments made by the user. These data are used to define the technology benefits/risks, value proposition and predictive market performance.

Benefits and Risks

The benefits and risks are first examined from the perspective of the medical efficacy and safety profile. Preferably, these benefits and risks are based on clinical trial data. The comparative degree of success in achieving clinical trial endpoints is relative to other technologies in the same therapeutic area with the same indication. An indication is a specific FDA approved use for the product. In the case of new technologies with no medical comparators, appropriate surrogate comparators for different indications with the same endpoints may be used. In the case of multiple clinical endpoints, the tool is capable of scaling the relative importance of different endpoints to each other in addition to scaling the relative importance of degree of effect within an individual endpoint.

Side effects are evaluated as risks which arise out of these trials and which express a risk score of certain frequency and severity that impact the feasibility of the innovation to meet regulatory approval and achieve marketplace success. As in the case of benefits, the significance of a result with an individual side effect and the relative importance of one side effect versus another can be scaled within the model.

Value Proposition

The medical benefits and risks are viewed from the perspective of a multi-stakeholder or technology user community. Community values are qualitatively or quantitatively generated and translated or framed within the context of the technology's core attributes. When joined together with the technology attributes, these values offer a consolidated score to predict commercialization success. Ideally, this score represents a consensus of the total value proposition of the technology for that entire community of technology users. The contribution of each particular stakeholder's needs for specific definitions of value is proportionately weighted and integrated into the total value proposition of the technology's attributes and drawbacks.

The range of stakeholder benefits and risks that result from the basic profile of the medical efficacy and safety of the innovation are broad, yet specific to the therapeutic area under evaluation. The community impacted by the technology will also play a critical role in the translation of benefit and risk as outlined with examples below:

Patients—Outcomes of therapy that impact physical, mental, emotional, and social functioning can be measured, weighted, and integrated.

Health Care Systems—Measures of quality and efficiency that improve value to those delivery systems involved in the delivery of care can be entered.

Payers (Employers/Governments)—Improving cost effectiveness and targeting patient populations to lower spending and increase value that will enhance employee or beneficiary productivity and improve health outcomes. Payers can also refer to the innovation developer, who, by applying certain strategies (e.g., utilizing biomarkers), will improve the efficacy for targeted subpopulations and therefore increase the likelihood of development and market success, resulting in a return on the research investment.

As in the case of the medical efficacy and safety factors above, the software tool allows for the individual and relative scaling of measures against each other. Furthermore, in the development of the value proposition, one other element is vitally important in creating an optimal risk/benefit profile. The tool mitigates risks through a function that allows for the subtraction of excessive side effect severity and/or frequency through marketplace interventions designed to ensure appropriate use of the product or control of product misuse or abuse.

These risk mitigators are scored commensurate with their value and capabilities to manage side effect risks, and can be adjusted up or down accordingly. They can include a number of established market-accepted factors to control risk such as patient registries, lab tests, physician certification, controlled distribution, and patient and provider education.

Market Dynamics

The third set of values comes from the application of the tool to the marketplace. This third set of commercialization factors are success predictors of the technology's application in the market and can be described by some of the following examples:

Ease of use—generally product formulation or presentation variables across a broad range of parameters from administration, to temperature to delivery to packaging.

Patient access—payment contribution based on payer demands and access restrictions.

Provider restrictions—healthcare deliverer (physician, nurse, care system) or system constraints due to payment, access, regulatory hoops or other considerations such as government coding or reimbursement requirements.

Market considerations—historical trends of the market, including past requirements for access and entry into top markets based on competitor success or failure for access.

Data from the three categories outlined above—technology benefits/risks, value proposition and market dynamics—can be relatively scaled against each other to present the most sophisticated assessment of the technology's total benefit and risk profile. Furthermore, the relative degree or market tolerance of risk versus benefit can also be assessed in the therapeutic category using the model-scaling feature.

Other aspects and embodiments of the invention are also contemplated. The foregoing summary and the following detailed description are not meant to restrict the invention to any particular embodiment but are merely meant to describe some embodiments of the invention.

BRIEF DESCRIPTION OF THE DRAWINGS

FIG. 4 to FIG. 30 are exemplary layouts for various screens useable to input information and output a scorecard and other summary information;

FIG. 31 and FIG. 32 show an exemplary comprehensive scorecard including several medical treatments being compared relative to the benefits and risks for success; and FIG. 32 shows an exemplary four-quadrant risk/benefit graph.

DETAILED DESCRIPTION

Figure 1:
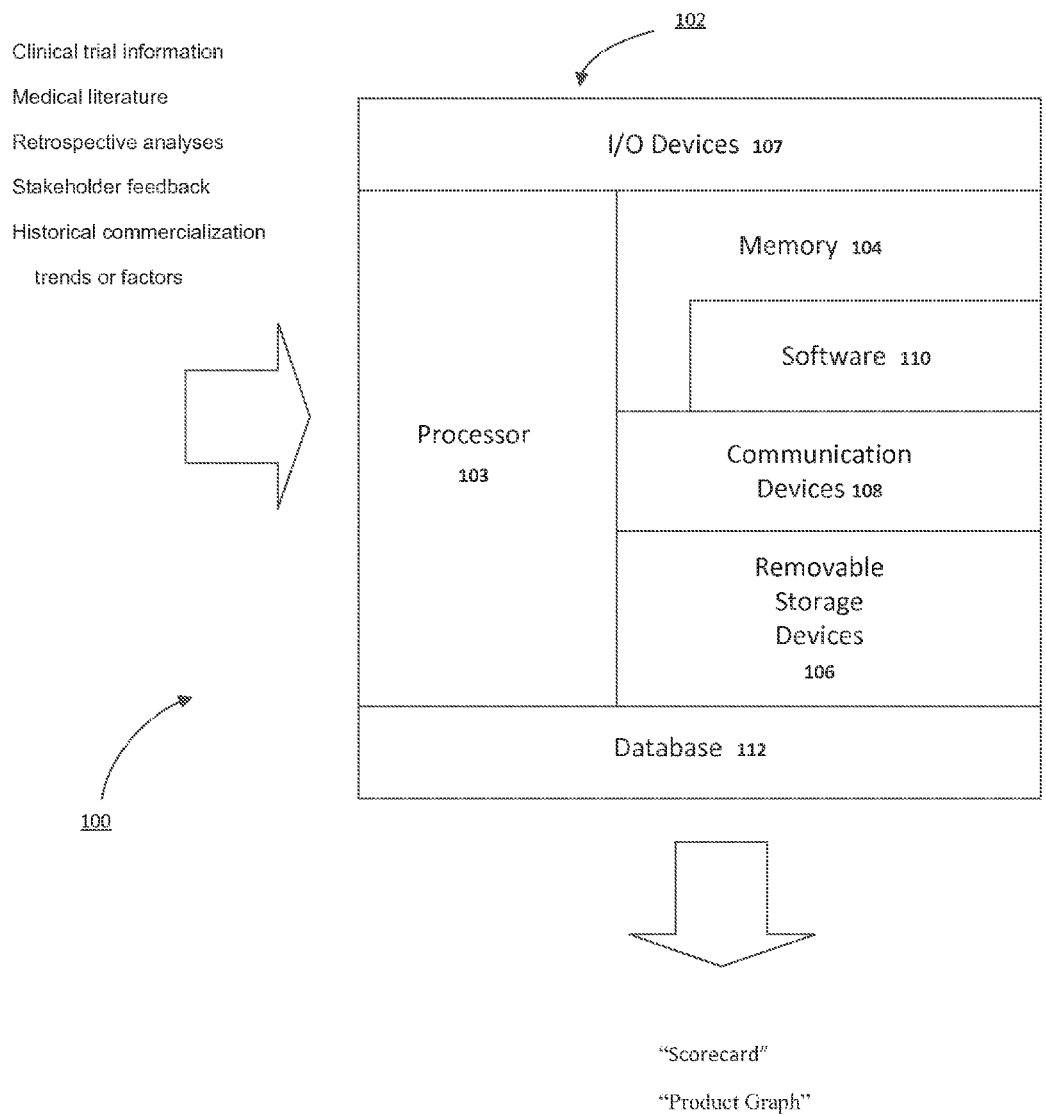
FIG. 1 illustrates an exemplary system useful for evaluating and comparing medical treatments, according to an embodiment of the present invention.

FIG. 1 shows an exemplary system 100 useful for evaluating and comparing medical treatments, according to an embodiment of the present invention. As illustrated the system 100 includes a computer 102 having a processor 103, memory 104 (RAM, ROM, etc.), fixed and removable code storage devices 106 (hard drive, floppy drive, CD, DVD, memory stick, etc.), input/output devices 107 (keyboards, display monitors, pointing devices, printers, etc.), and communication devices 108 (Ethernet cards, WiFi cards, modems, etc.). Typical requirements for the computer 102 include at least one server with at least an INTEL PENTIUM III processor; at least 1 GB RAM; 50 MB available disc space; and a suitable operating system installed, such as LINUX, or WINDOWS 2000, XP, Vista, 7, 8 by Microsoft Corporation. Representative hardware that may be used in conjunction with the software of the present invention includes the POWER EDGE line of servers by Dell, Inc. and the SYSTEM X enterprise servers by IBM, Inc. Software 110 to accomplish the methods described below may be initially stored on a non-transitory computer-readable medium (e.g., a compact disc) readable using one of the fixed and removable code storage devices 106 or transmitted as an information signal, such as for download. The software 110 is then loaded into the memory 104 for execution by the processor 103. A database 112 used to store information can include any computer data storage system, but, preferably, is a relational database organized into logically-related records. Preferably, the database 112 includes a Database Management System (DBMS) useful for management of the data stored within the database 112. Representative DBMS that may be used by the present invention include Oracle Database by Oracle Corp., DB2 by IBM, and the SQL Server by Microsoft. The database 112 can either be a centralized or a distributed database. Alternatively, the database 112 can include an organized collection of files (e.g., in a folder).

Figure 2:
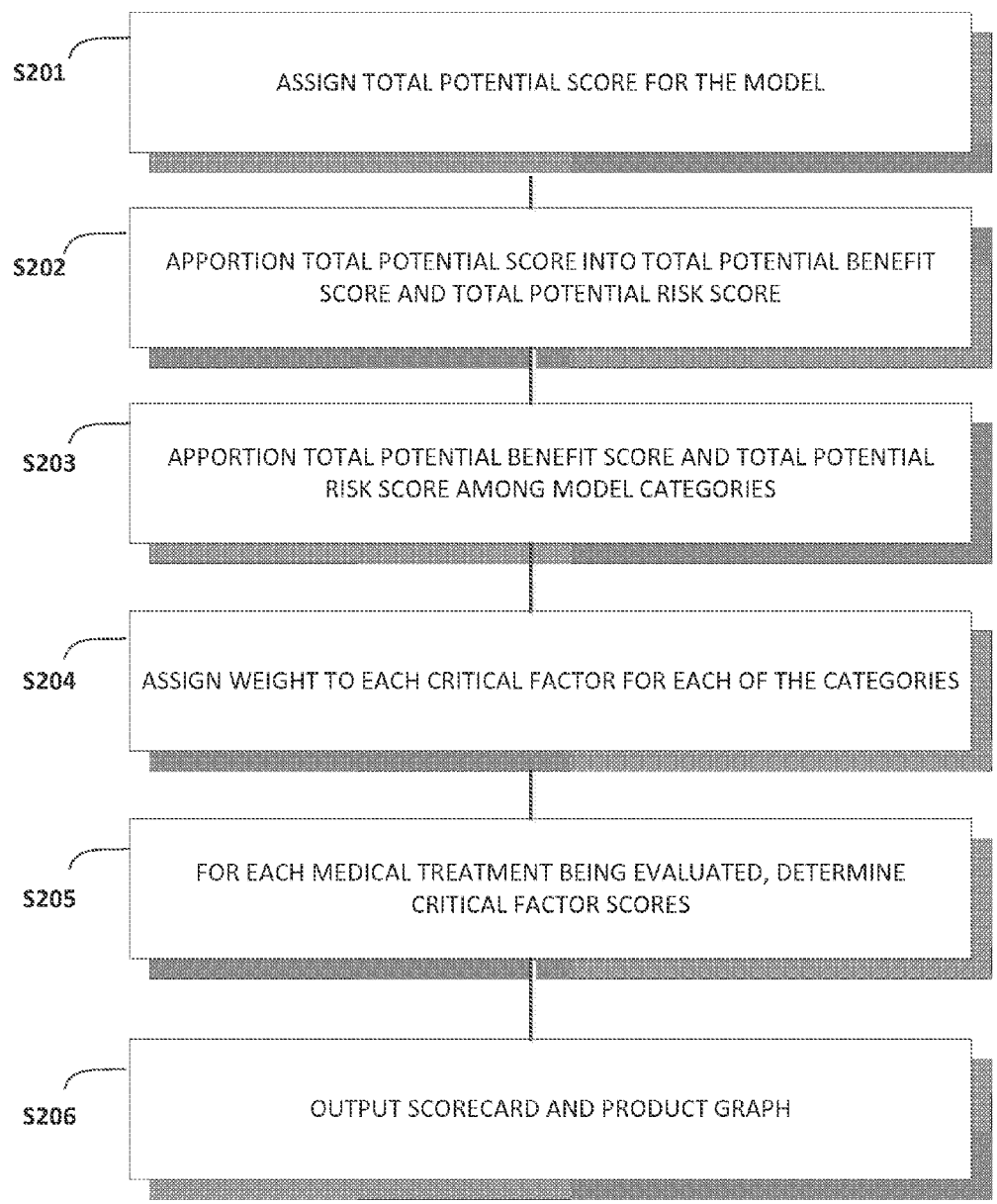
FIG. 2 illustrates an exemplary method for evaluating and comparing medical treatments, according to an embodiment of the present invention.

FIG. 2 shows an exemplary computer-implemented method 200 for evaluating and comparing medical treatments, according to an embodiment of the present invention. In a preferred embodiment of the present invention, the present invention comprises the computer system 100 including the memory 104 that stores one or more code segments (i.e., a computer program) including the software 110 of the invention executable by the computer 102. When executed on the computer 102, the present invention essentially transforms the computer 102 into a software tool that can perform the method 200.

It is to be understood that the method steps illustrated herein can be performed by executing computer program code written in a variety of suitable programming languages, such as C, C++, C#, Visual Basic, and Java. It is also to be understood that the software of the invention will preferably further include various Web-based applications written in HTML, PHP, Javascript and accessible using a suitable browser (e.g., Internet Explorer, Mozilla Firefox, Google Chrome, Opera).

Referring to FIG. 2, initially, in step S201, a total potential score 205 is assigned for the model. By way of an example, we have chosen the total potential score 205 to be "300"; however, another value could have been chosen.

In step S202, the total potential score 205 is apportioned, according to a first predetermined ratio 206, into a total potential benefit score 207 and a total potential risk score 208. The first predetermined ratio 206 is a benefit/risk ratio assigned to the model. It can be assigned as a preset value or by allowing the user to input the value (or for the user to override the preset value). In the example, given a 2:1 benefit/risk ratio, the total potential score 205 ("300") would be apportioned into a total potential benefit score 207 of "200B" and a total potential risk score 208 of "100r". (Here, the suffix "B" refers to "Benefit" and the suffix "r" refers to "risk").

In Step S203, the total potential benefit score 207 is apportioned, according to a second predetermined ratio 209, among each of a plurality of predetermined categories 210 to arrive at a total potential benefit category score 211 for each of the predetermined categories 210. Additionally, the total potential risk score 208 is apportioned, according to a third predetermined ratio 212, among each of a plurality of predetermined categories 210 to arrive at a total potential risk category score 213 for each of the predetermined categories 210. E.g., given a 5:3:2 ratio for the categories 210 "Medical Efficacy & Safety", "Value Proposition", and "Reimbursement & Administration", the scores would be: "100B, 50r" (Medical Efficacy & Safety), "60B, 30r" (Value Proposition), "40B, 20r" (Reimbursement & Administration). The second predetermined ratio 209 and the third predetermined ratio 212 can be assigned as preset values or by allowing the user to input the values (or for the user to override the preset values).

In Step S204, for each of the predetermined categories 210, a plurality of critical factors 214 associated with each of the categories 210 are assigned a risk/benefit classification 215 and a critical factor weighting 216. The critical factor weighting 216 can be assigned as a preset value or by allowing the user to input the value (or for the user to override the preset value).

In Step S205, for each of a plurality of medical treatments 217, a critical factor score 218 for each of the predetermined critical factors 214 is determined, the critical factor score 218 calculated using an input value (e.g., entered by a user via a screen) or a preset value, and if the critical factor 214 is classified as a benefit, the total potential benefit score for the category associated with the critical factor weighted by the critical factor weighting; or, if the critical factor is classified as a risk, the total potential risk score for the category associated with the critical factor weighted by the critical factor weighting. Information used to arrive at the critical factor score 218 can come from a variety of sources, including, clinical trial information, medical literature, retrospective analysis, stakeholder feedback, and historical commercialization trends/factors, etc.

In Step S206, a "scorecard" 219 is outputted. The scorecard 219 can include a row for each of the medical treatments 214, each of the rows including one of an indicia (e.g. a color code) and a numeric value for each of the critical factor score 218, for each of the categories. Additionally, a product graph can be outputted showing a total benefit score 220 and a total risk score 221 for each of the medical treatments 214 plotted thereon.

It is to be understood that the preceding description is meant to be illustrative, not limiting. Furthermore, it is to be appreciated that certain of the steps outlined above can be performed in an order different from the illustrated method. For example, the step S204 could be done prior to S203.

Part I: Model Schematic

In the following discussion, exemplary screen shots of the software tool are provided to illustrate its functionality. However, it is to be understood that the examples provided herein are not meant to be limiting. By way of example only, and as described herein, the software has been populated with data for three therapeutic drugs for substance use disorder (e.g., addiction to cocaine). TA-CD is a new drug with no competitor on the market in its class. As discussed earlier, in the case of new technologies with no medical comparators, appropriate surrogate comparators for different indications with comparable endpoints may be used. In this example, TA-CD is compared to SUBOXONE (registered trademark of Reckitt Benckiser Healthcare (UK) Limited) and VIVITROL (registered trademark of Alkermes, Inc.). This illustrates how the software tool can be used to predict the value proposition for first in class entries into the marketplace. It is to be understood, however, that various other drugs/treatments could be evaluated for a variety of different diseases/disorders, and that the present invention has general applicability to various treatment comparisons.

Figure 3:
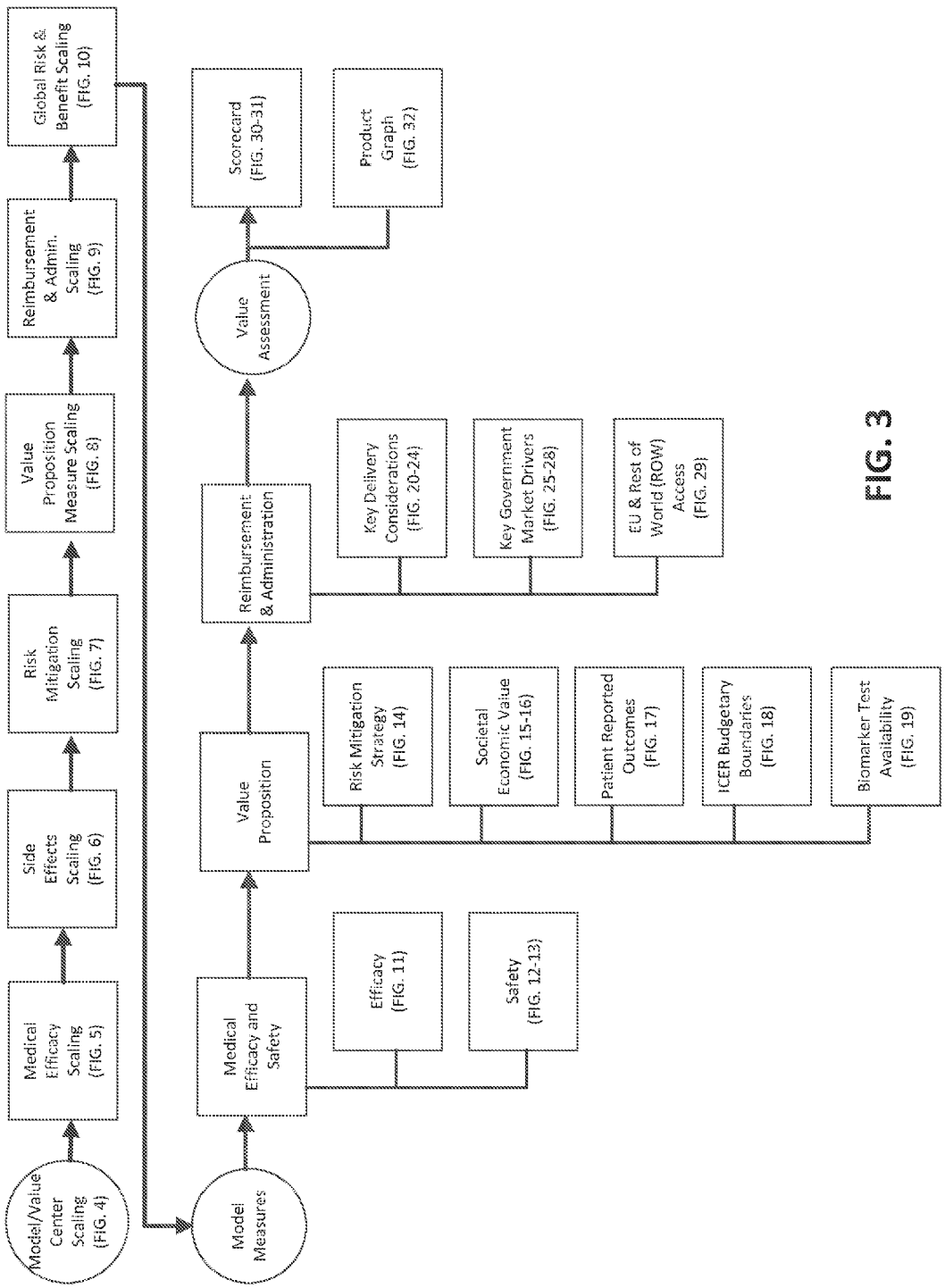
FIG. 3 illustrates a schematic including exemplary model elements of the present invention.

Details of each schematic element follow the schematic diagram shown in FIG. 3. The following points are worth emphasizing (1) most schematic elements can be populated independently of other elements; (2) each element has an associated score value, for either the "B" benefit or "r" risk for overall asset scoring relative to comparators; (3) overall asset development scores can be accumulated as the elements are completed; (4) comparator assets are also loaded into the model. In regard to the last point, since their attributes are already known from their completed development and commercialization programs, the comparator assets can be scored more easily for their resulting benefit-to-risk scores. These scores are on the "scorecard" that drives the relative market positioning on the final screen graph.

Part II: Model Scalings

The purpose of the scaling screens shown in FIG. 4 to FIG. 10 is to weight the importance of measures used in the model relative to each other. In some instances, the values entered will override preset values. It is to be understood that the assigned scalings reflect user judgments and users of the software tool could obtain profoundly different results (e.g., scorecards) depending on how the scalings are initially established. However the benchmark products, that is, those operating in the marketplace today, have achieved or not achieved commercial success. Therefore if the model is not calibrated with these comparators falling in their appropriate quadrants on the four-quadrant graph, the subjectivity of the scalings is overriding the model's preset accuracy.

Figure 5:
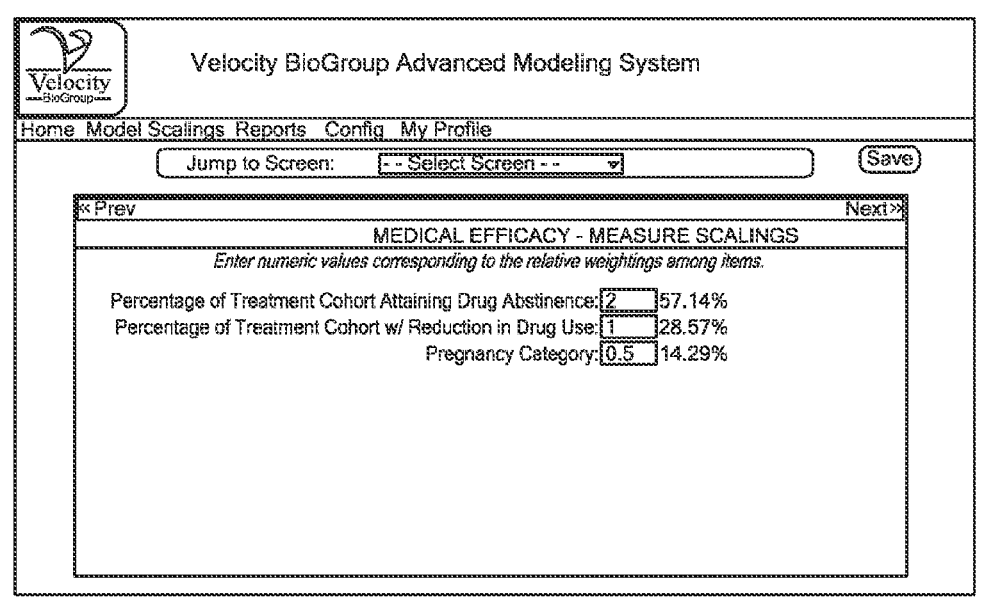

Value Center Scaling (FIG. 5)

The Value Centers describe the three jurisdictional areas that encompass the core attributes of a drug, vaccine, or medical device:

Benefits and Risks—Medical efficacy and safety are defined by results from clinical trials or information derived from retrospective reviews of data from technologies in the marketplace. These measures are described in greater detail elsewhere.

Value Proposition—To what extent can the asset be developed to meet the specific needs of payers, health care service delivery providers, (such as hospitals, health plans, long term care, insurers), patients, caregivers, and governments? These opportunities to translate medical efficacy into stakeholder-specific values, or mitigate safety concerns for similar stakeholder intent, are all configured into the value proposition. These translations can include regional, national, and global requirements for value presentation that may in turn affect reimbursement and access in each jurisdiction.

Market Dynamics—Reimbursement, administration, and access define marketplace dynamics that may pose challenges for payment to providers and patients. The data captured identifies how public and private payers will affect the technology access through their reimbursement systems, including coding, formulary tiers, prior authorization, co-pays or co-insurance, step edits, and guideline/use protocols. The model is constructed to adjust for both US and global inputs.

In the case of the substance use disorder compounds compared in the example model described herein, it was determined that medical efficacy was a higher predictor for commercialization success than both the development of a value proposition and the reimbursement, administration and access factors (leading to a 4:3:3 ratio.)

Medical Efficacy Scaling (FIG. 5)

The scaling screen for medical efficacy acknowledges that not all efficacy measures are considered equal to health care service providers. Although the Food and Drug Administration (FDA) may traditionally require only one clinical endpoint to measure efficacy, the market may simultaneously value more than one. Additionally, if the science is leading to the emergence of new endpoints to measure efficacy, these new measures may have arising but less established or validated value. One good example is illustrated above in the model in the comparative weight of the abstinence endpoint versus the reduction in use endpoint. Traditionally, abstinence was a singular measure of medical efficacy for substance use trials; today the FDA, health care providers, and payers are beginning to realize the medical benefits of the impact of reducing drug use on overall health outcomes. Some of these outcomes include: reduction in HIV/AIDS transmission, the spread of Hepatitis C, and emergency room visits. Although abstinence is the ultimately desired goal, reduction in use has recently been recognized as a significant and important efficacy measure (thus the 2:1 ratio, as shown). Additionally, the FDA Pregnancy Category classification for the technology is included as part of the values weighted in either the medical efficacy or safety screens. Although it is not a clinical measure, results in the Pregnancy Category can profoundly affect use on specific populations, (i.e., those of childbearing age), which may be very important to the product's success or failure in the marketplace. Category A or B ratings may positively impact the medical efficacy profile in the marketplace, while Categories C, D or X may be viewed as serious side effects and have a significant impact on commercialization.

Figure 6:
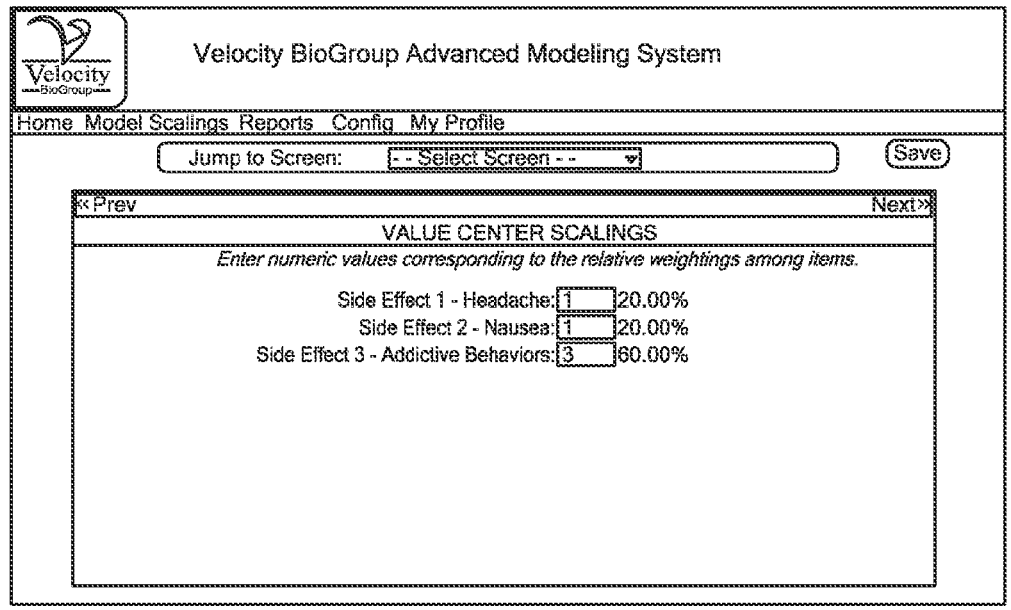

Side Effect Scaling (FIG. 6)

Not all side effects are created equal, even adjusting for frequency and safety variability. Depending on the therapeutic category, and especially the competition of other therapeutic agents within the class, side effects are critical determinants of a product's risk/benefit ratio and its likelihood of commercialization success. The scaling property of the software tool gives the user the ability to adjust for the prioritization of these side effects specific to the demands of the therapeutic category. In order to recognize the impact of these side effects on patients, health care providers, payers, and the FDA's perception of drug approvability, the comparative value of the new intervention relative to older treatment alternatives must be considered. Furthermore, some side effects may be interwoven with the intervention. For example, in the case above, TA-CD has a relatively high frequency of headaches, but withdrawal from cocaine is also similarly associated with a high headache frequency. Therefore its significance as a side effect is less important.

The side effect defined as addictive behaviors comprises not a single measure, but a constellation of measures. This illustrates how the software can capture the complexities of a therapeutic category and the challenges associated with it. In the case of addictive behaviors, addicts can become permanently addicted to their medicines or sell their medications on the black-market. This has resulted in a well-known and very troublesome side effect consequence, and hence a priority to the health care community, as represented by the software scaling (1:1:3 ratio).

Figure 7:

Risk Mitigation Scaling (FIG. 7)

The Risk Mitigation scaling screen is intended to address two components of the mitigation of side effects: actions that reduce the severity of the risk and actions that create a positive or negative commercial impact.

First, mitigations can directly reduce the severity and frequency of side effects, though the model makes these adjustments to the total risk score by subtracting from the severity multiplier. This is depicted here under "Mult" (for multiplier) whose values can be adjusted through a series of additive risk mitigation actions. The values for the set of actions taken are subtracted in total from a single side effect severity multiplier. (This total cannot exceed a designated amount.) It is important for these adjustments to remain consistent across all comparators in the model, including the proposed new innovation. These scores should determine on a case-by-case basis what the likely impact of the proposed risk mitigation intervention would be on the side effect in question.

For example, with respect to substance use disorder drugs, patient contracts for misuse are an important way to "pledge" patients for appropriate use and to help prevent drug diversion, overdose, and/or misuse. These contracts are far more effective, however, if they are also accompanied by an intensive patient education program, which is also a risk mitigation strategy. In the case of the new innovation, TA-CD, patients on the new therapy have been shown to ingest more than the normal dose of cocaine in order to try to override the vaccine's effect. Again, to protect against the potential for the TA-CD side effects, it is necessary to educate the patients in advance of therapy initiation about how the vaccine works and why they must commit to the therapy with a contractual understanding that there is "no going back on their therapy commitment."

Secondarily, in the right column called "Add," the software adjusts for the commercial impact of the proposed risk mitigation strategies on market access and reimbursement. For example, patient registries can positively control misuse and mitigate potential adverse reactions; however, many physicians will not write prescriptions for technologies that they must manage through a registry because of the concomitant time and paperwork demands. In this case, the subtraction from the multiplier (by use of a patient registry) that reduces side effect risk and therefore lowers risk score can also be adjusted as an addition or subtraction to the risk score using the right hand scaling column to account for the potential negative or positive impact to commercialization.

Value Proposition Measure Scaling (FIG. 8)

This scaling screen weights the spectrum of value proposition factors that can translate the medical efficacy and safety factors of the software into viable value proposition components for payers, health care systems, and patients. This "translation" involves the development of specific tools and secondary clinical trial endpoints that will paint a comparative picture of the asset's capabilities to deliver this specific value proposition relative to that of the competitors under consideration.

In the case of the model presented above, the components of the translation include those elements of the new technology that present an economic value proposition to payers, particularly in terms of the current standard of care. Since drug abuse is a costly societal problem, the scaling weights are adjusted to reflect these economic impacts. Additionally the software tool recognizes international development: these assets use the Incremental Cost Effectiveness Ratio (ICER) for evaluations in Europe through the National Institute for Clinical Effectiveness (NICE) by considering their budgetary boundaries for product reimbursement and access. In the example presented here, arrests, re-incarceration, and physician clinic use are all substance use disorder markers for creating secondary endpoints for the disproportionately high numbers of cocaine addiction sufferers who enter the criminal justice system and require treatment.

Finally, the last four components of the scaling chart are measures of patient-reported outcomes that are used as secondary endpoints to assess the impact of the treatment intervention on the wellbeing and quality of the patient's life.

Reimbursement & Administration Scaling (FIG. 9)

Market dynamics include a wide array of factors that impact the commercial success of a new technology. It must include the perspectives of the patient, clinician, and payer. The patients and providers determine the proper scaling for use and administration. Oral formulations are generally preferred over injectable formulations for the patient. For the provider, route of administration can impact reimbursement from payers and plays a significant role in determining product choice. Scaling for the payer is focused on cost savings from a "systems" perspective in the private market and the societal costs in a public market. These marketplace dynamics are critical to the overall assessment of the value proposition for the new technology.

Figure 10:
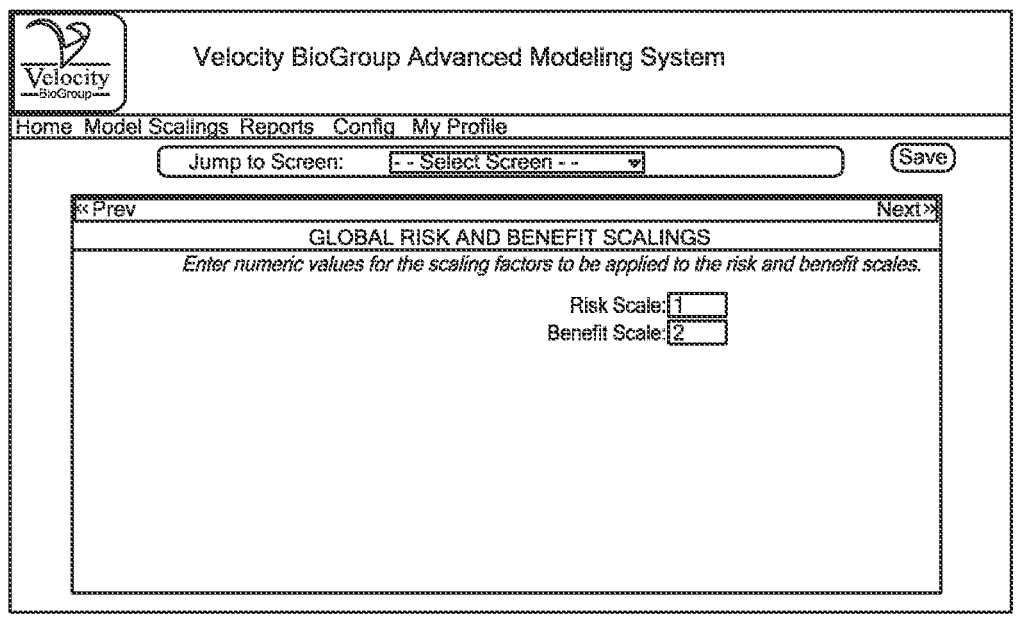

Global Risk & Benefit Scaling (FIG. 10)

The global risk and benefit scaling is the highest-level assessment in the model. It is here that the user determines the relative weighting of risk and benefit for the therapeutic category of the asset under consideration. This ratio between the risk and benefit is again very specific to a therapeutic category in question; for the products in this example for substance use disorder, the relative benefit risk ratio is 2 to 1 based on the lack of effective treatment interventions in the marketplace. The ratio recognizes not only the limited biopharmaceutical competition in existence today but also the limitations of the alternative treatments currently in use, including the enormous medical, personal, and societal costs associated with less-than-optimal treatments.

Part III: Critical Factors

Medical Efficacy & Safety

Figure 11:
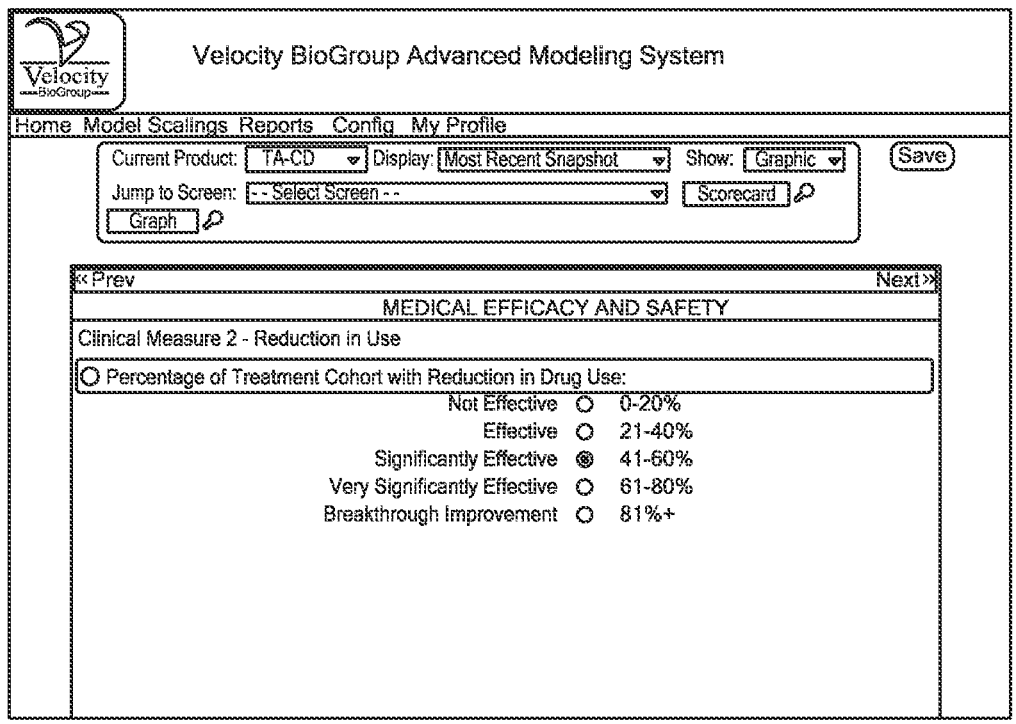

A. Efficacy (FIG. 11)

The clinical efficacy measures are measures or metrics of what a new drug, vaccine or medical device does that is efficacious or capable of producing the intended effects. In the software tool these measures are assigned levels of significance to specific FDA-required or proposed primary endpoints. In the example of the substance use disorder vaccine above (TA-CD), "reduction in use" is one such efficacy measure. Here, the model presents comparisons of efficacy values achieved by the target drug (or vaccine) in the clinical development program against two comparators currently in use in the marketplace. (See top of screen for pull-down menu item "Current product" tab in the floating blue box. This is used to alternate between the comparator drugs, in this case Suboxone® and Vivitrol®, loaded as comparators.) In the example above, the percentages refer to the percentage-of-substance-use reduction for the substance of abuse in question as defined by the clinical trial parameters. Multiple screens can be created to capture all efficacy measures related to the therapeutic class under review. The levels of significance are unique to the therapeutic area and are established by the stakeholder community's assessment. Generally for medical measures, the body of relevant physicians will determine the significance of achieved results; however, any relevant stakeholder in the healthcare value chain can assign value to these trial efficacy measures. Each level of significance has a specific benefit score assigned to it that then becomes a component of the total cumulative score of total benefit in the model scorecard.

B. Safety

Figure 12:
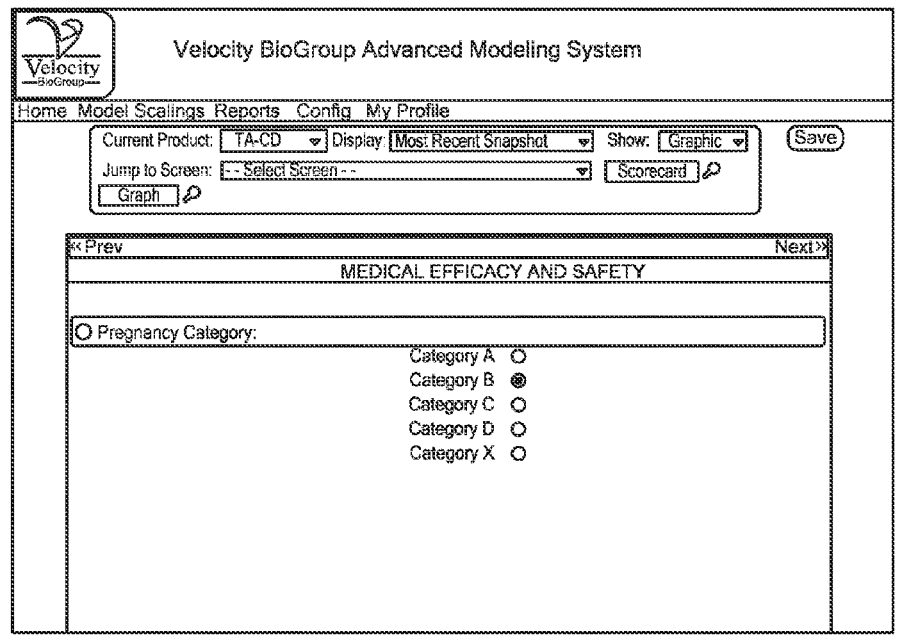

Pregnancy (FIG. 12)

The FDA Pregnancy Category classification rates the relative safety of new innovations on unborn children that reflects the perceived risks of use of a product on women of childbearing age. These designations can have a significant effect on usage depending on the therapeutic category in question. Some of the categories, (such as Category X) are so onerous as to create the need for extensive risk mitigation plans. In the case of the example product above, TA-CD is forecast to be relatively benign in pregnant women (Category B) relative to the Category C rating of its comparators, meaning that the TA-CD has not demonstrated untoward effects on the unborn in animal clinical trial models. This could be particularly relevant for drug addicts who are often young women.

Figure 13:

CIOMS Classification (FIG. 13)

This safety screen of the model reflects two components of a risk score, with both components expressed in terms defined by the Council of International Organizations of Medical Sciences (CIOMS), Workgroup IV in 1998. This international body set standardized definitions for frequency and severity of side effects, that are now commonly used in clinical trials by the biopharmaceutical industry and are used in this example herein. The frequency component of the safety measures are multiplied by the severity component to yield a total risk score. Although frequency rates for occurrence are quantitative measures across all diseases states, severity ratings are qualitative in nature. In other words, depending on the specific disease state and comparator medicines in use, the tolerance for a particular side effect varies from product to product and must therefore have a significance rating relevant to the specific stakeholder community. This usually includes the physician community, but payers, health care systems, and patients can all play a role in this evaluation. In the case of TA-CD, headaches often accompany withdrawal from drugs of abuse, and hence this side effect is considered to be frequent. Additionally, the effect is not viewed as particularly consequential within the context of the addiction being treated; i.e., the risk/benefit ratio warrants the product usage.

Value Proposition

Figure 14:
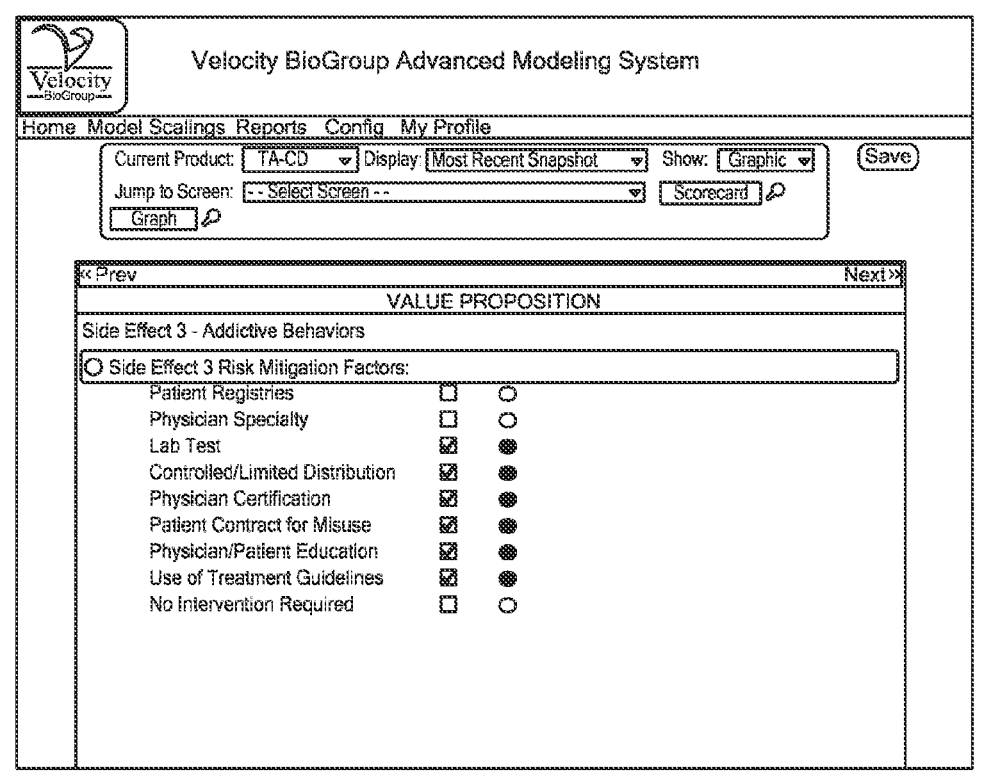

A. Risk Mitigation Strategy (FIG. 14)

Risk mitigation strategies have become increasingly important in the management of the risk/benefit ratio of emerging health care interventions. Companies that do not actively plan these strategies for their new technologies face both marketplace and regulatory approval peril. Within the current environmental context, both the FDA and payers now view risk over benefit as the tipping point in health technology assessment. The software model presents the principal risk mitigation options available. By choosing specific interventions, the frequency and severity of side effects can be reduced and integrated into the overall value proposition for the product. The impact of the risk mitigation intervention on the risk score is adjusted by subtracting the intervention values from the multiplier values of the severity scores of the related side effects. This action lowers total risk by assuming that the intervention will lower side effect severity; in reality, the risk may be lowered by a decrease in the frequency of side effect occurrence as well.

In this example, particular interventions have been chosen to offset the specific side effects of TA-CD. All of the presented strategies have the potential to offset the addict's tendency to try to overcome the product's capability to block the reward effects of the drug of abuse. The goal is to create an optimized approach to risk reduction that mitigates safety concerns without significantly compromising optimized product use potential. This selection process takes into account the specific risk mitigation strategies of the comparator products that may "benchmark" expectations with the FDA (or possibly have been previously mandated by them), with healthcare providers and with payers and their delivery systems.

In the example above, lab tests are generally used to measure drug toxicity, but in this case, the lab test is performed on a periodic basis to ensure that the drug user is not returning to the use of the substance of abuse. Excessively high metabolites of cocaine in the urine would indicate that the patient is attempting to override the blockade of the vaccine. Since lab tests for drug use are frequently part of addiction treatment programs, the intervention is not considered a commercially onerous intervention, although its impact on reducing risk could be significant.

Figure 15:
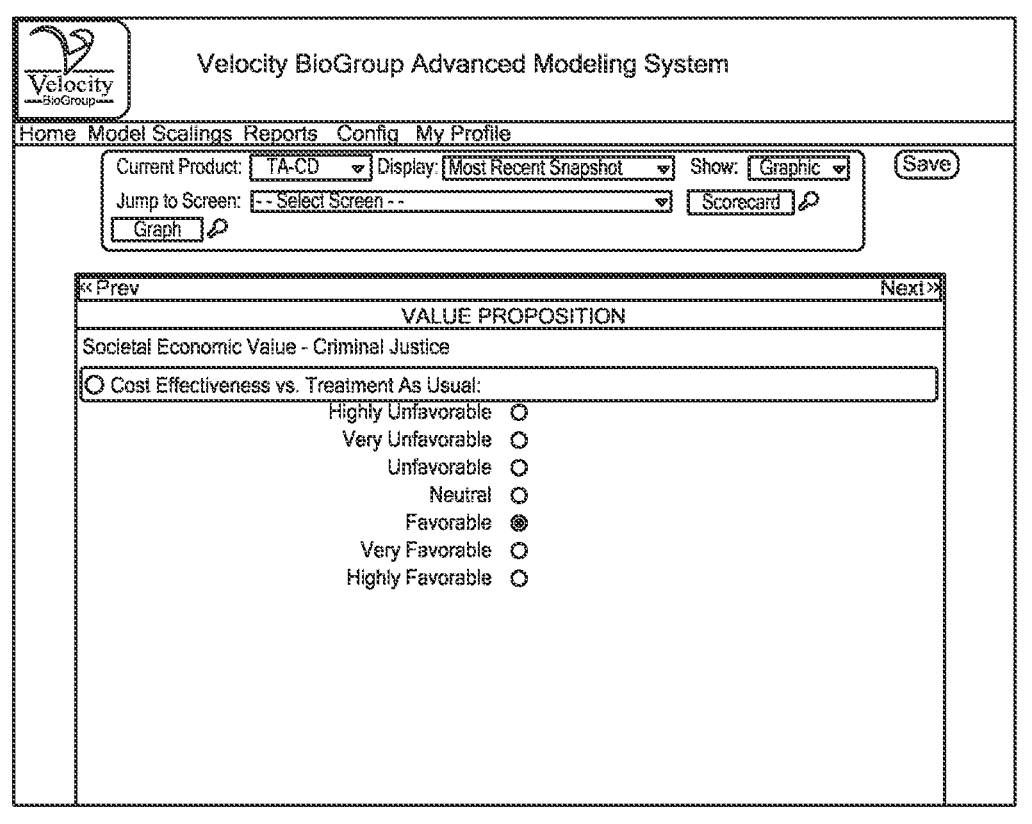
Figure 16:
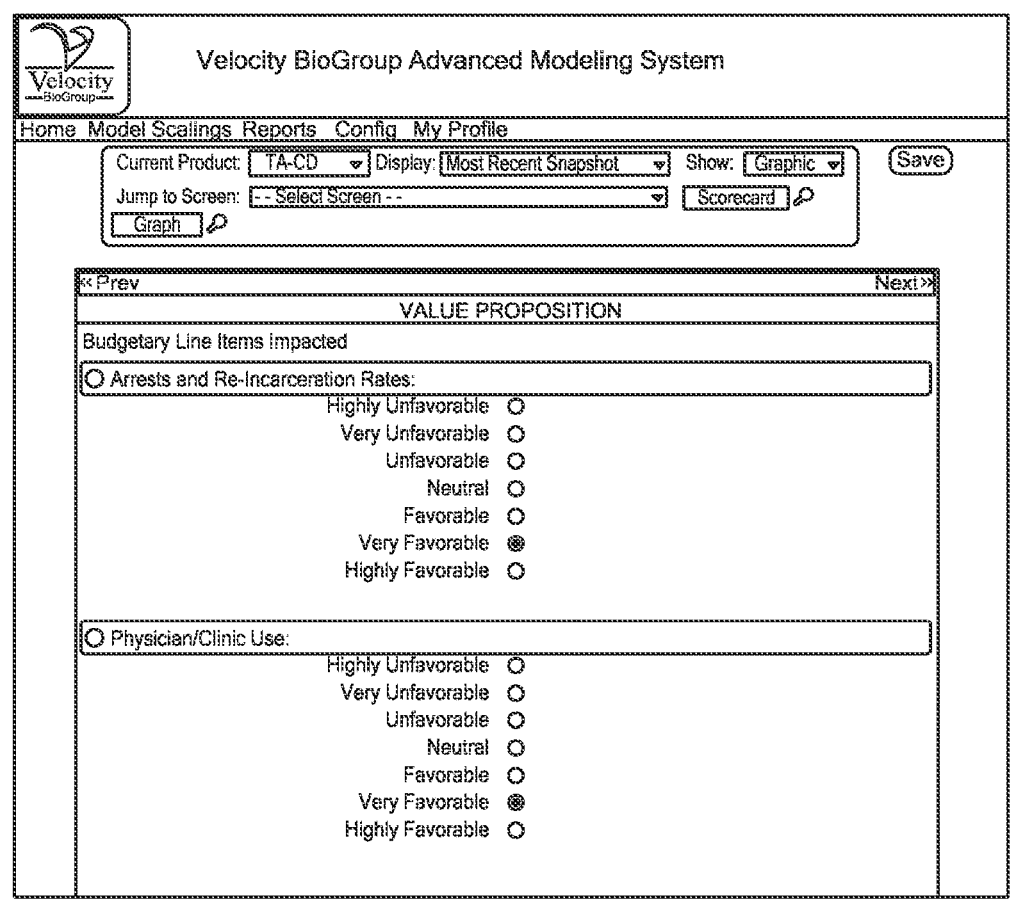

Societal Economic Value (FIGS. 15-16)

The value proposition section considers critical areas where the medical efficacy and safety factors of the asset can be translated into viable value proposition components for payers, health care systems, and patients. This "translation" involves the development of specific tools and secondary clinical trial endpoints that will paint a comparative picture of the asset's capabilities to deliver a specific value proposition relative to that of the competitors under consideration.

In the case of the example presented above, an economic value proposition to payers, particularly in terms of the current standard of care, is best translated by looking at the cost effectiveness of TA-CD as compared to the impact of other treatment interventions for substance use disorder. TA-CD has no direct comparators since it is first to market in this therapeutic class. However, since drug abuse is a costly societal problem, the model chooses economic determinants of value in secondary endpoints to further translate benefits of the product. These will probably be followed in late stage development with more specific translational tools of economic assessment that measure impact on total system expenditures following the use of TA-CD, including "broader" societal costs of reduced criminal justice outlays for crime, treatment, incarceration, and justice system processing.

The value proposition that translates medical efficacy into specific data points using arrest frequency, rates of re-incarceration, and physician or clinic use tracks with value proposition development of other drugs of abuse. These are primarily markers for economic benefit; however, they also represent medical and societal benefit to large payers such as governments (state and federal) and employers. In the case of substance use disorder, federal and state arrests for trafficking and use of illicit drugs is high, creating a considerable financial burden to correctional systems. Therefore, the viability of creating a value proposition around these markers is a strong indication of marketplace success.

Figure 17:
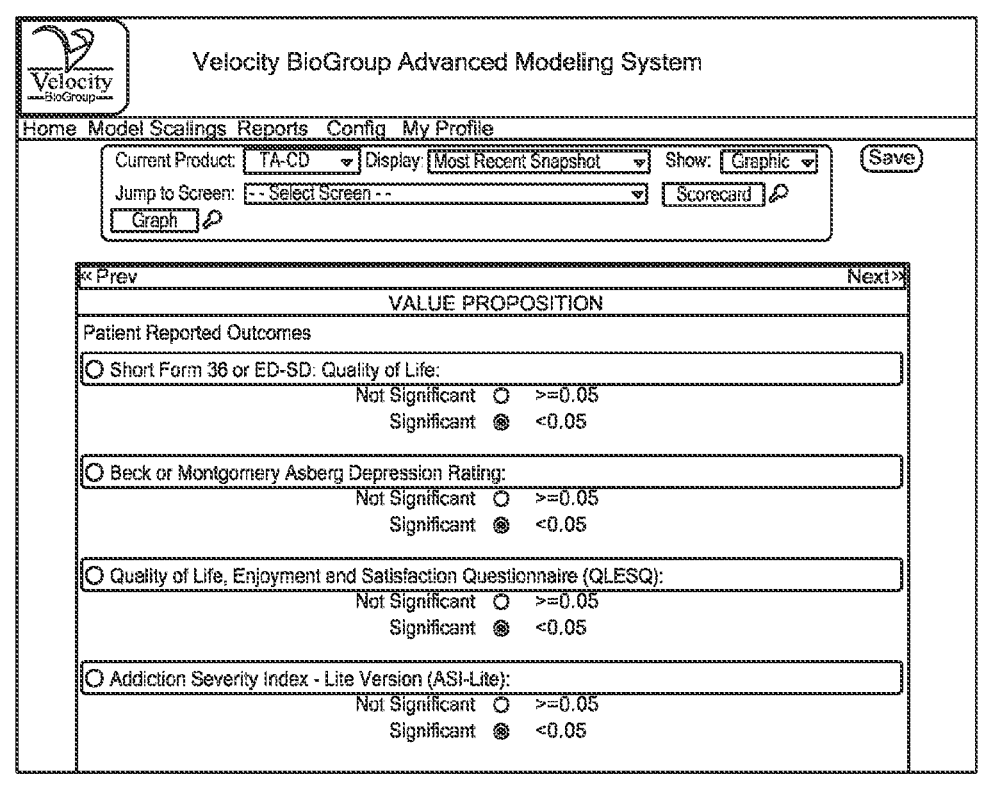

Patient Reported Outcomes (FIG. 17)

Patient (or caregiver) reported outcomes (PROs/CROs) represent a broad spectrum of tools that defines value from the perspective of technology users or those who care for these patients. If strategies for using these tools are discussed and negotiated with the FDA at an earlier stage of development, they can be used as part of the promotional label of the biopharmaceutical or device at the time of its approval and thus support commercialization goals. Furthermore, PROs/CROs can support the clinical package by framing the impact of a medical intervention on a patient or caregiver's overall quality of life, including physical, emotional, social, and cognitive impacts.

In the case of TA-CD illustrated above, four tools are used to evaluate these dimensions of quality of life. The SF36, ED50, QLESQ and the ASI Lite are all designed to measure these multi-dimensional elements of patient improvement, with ASI-Lite being specific to addicts. The depression tool is intended to capture the impact of the intervention on quality of life from the perspective of a generalist tool that will evaluate the emotional domain of quality. This tool selection was based on a knowledge of the mechansim of action of TA-CD as well as an understanding of its clinical and stakeholder benefits.

Figure 18:
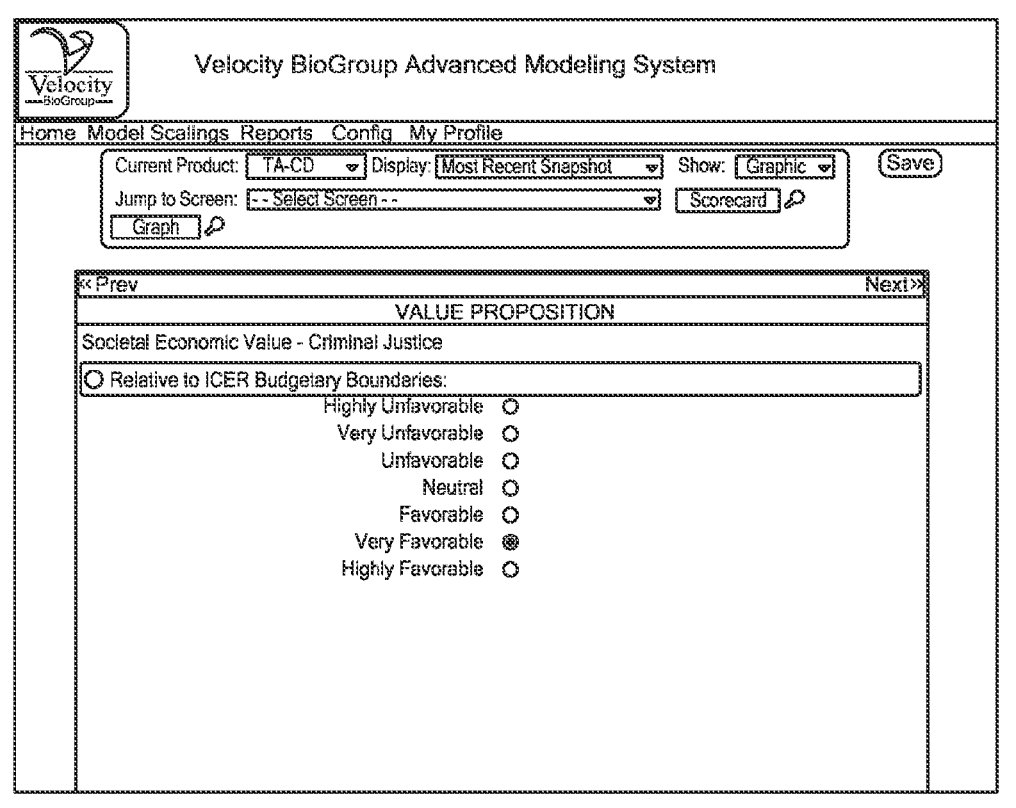

ICER Budgetary Boundaries (FIG. 18)

In the development of the economic value proposition for payers, the software tool supports international as well as US development by using the ICER for calculating budgetary constraints in European markets. The ICER is calculated and assessed through NICE in the United Kingdom, which then determines whether their National Health Service will reimburse for the new technology based on its incremental value contribution to their countrywide health care system. The ICER is currently set at approximately US$50,000.

In turn, other European countries will use the results from NICE and make their own translations of this analysis. By considering these budgetary boundaries for product reimbursement and access, the software user can predict whether a value proposition can be developed from the clinical data that can support its commercialization success in a major market beyond the US. The software tool can be customized to reflect many such government or private sector budgetary tools that determine value based on a set of evaluative criteria. In the case of TA-CD, the "very favorable" rating for ICER reflects the ability of the product to impact medical treatment as well as social costs, especially within the context of the limited options currently in the marketplace.

Figure 19:
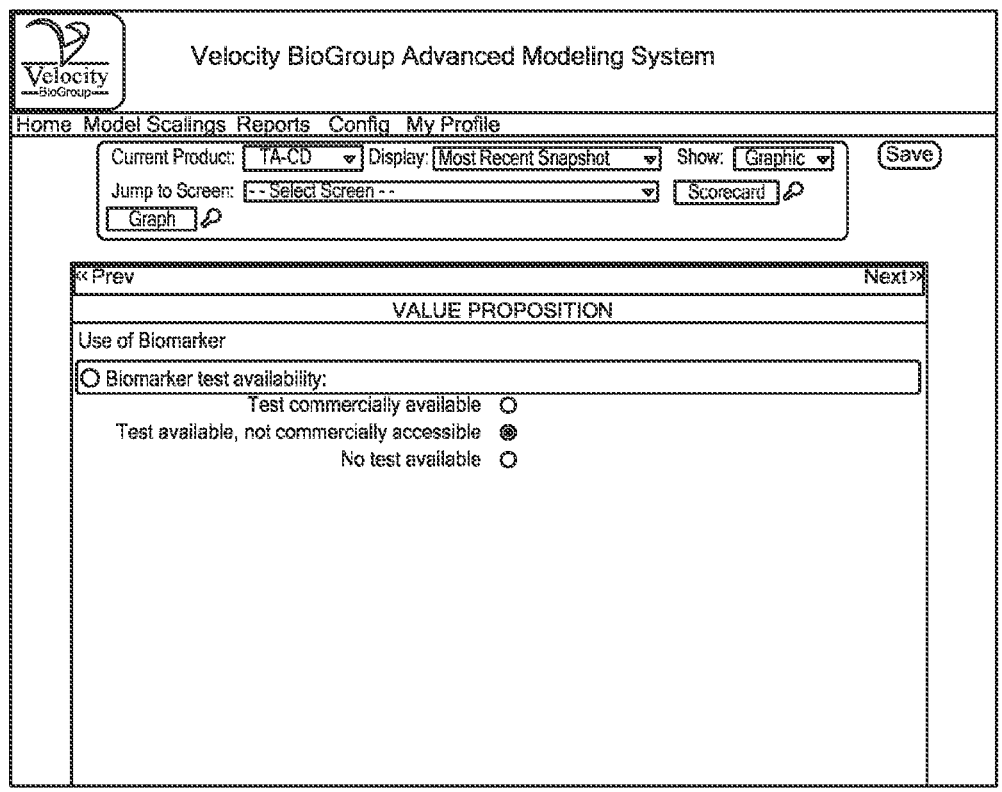

Biomarker Test Availability (FIG. 19)

A biomarker or biological marker is defined as a characteristic that is objectively measured and evaluated as an indicator of normal biological processes, pathogenic processes, or biological responses to a therapeutic intervention. See, Biomarkers Definitions Working Group (2001), Clinical Pharmacology and Therapeutics, 69, pp. 89-95, which is incorporated by reference herein in its entirety. Included in this definition is a genomic biomarker that is a DNA and/or RNA characteristic that is an indicator of normal biological processes, pathogenic processes, and/or response to therapeutic or other interventions.

It is now understood that biomarkers will play a significant role in value proposition development as well as cost-effective innovation delivery. Biomarkers can reduce uncertainty in drug, biologic or device use by providing quantitative predictions about their performance. Biomarkers can translate generalized study results into superior efficacy outcomes and reduced risks for subpopulations revealed by the markers. These can include patient subgroups with specific genetic deficiencies or those with surrogate endpoints revealing predictors for product efficacy or safety failure.

In the case of TA-CD approximately 25% of patients who smoke "crack cocaine" fail to produce specific antibodies for the cocaine vaccine. This is due to the production of natural, non-specified antibodies in response to the hot crack splinters in the lungs of patients that create an innate immunological response. These antibodies however, known as the IgM type, prevent the cocaine antibodies specific to the vaccine from forming and are therefore predictors of a patient subpopulation for whom the vaccine will not be effective.

The biomarker to predict the presence of the IgM antibody type is a simple blood test for its measurement. Given that the vaccine already presents certain challenges for efficacy, the elimination of any factors reducing response rates has enormous significance in the creation of the value proposition.

These improved effects on efficacy can, in turn, increase cost effectiveness, patient outcomes, quality of care metrics and payer or reimburser acceptance.

Reimbursement & Administration

A. Key Delivery Considerations (FIGS. 20-24)

Figure 20:

One of the key components of the success of a new technology in the marketplace is the functionality of the product in its delivery system. For a vaccine, this crosses a wide spectrum of delivery considerations including reconstitution and its stability at room temperature (FIG. 20).

Figure 21:
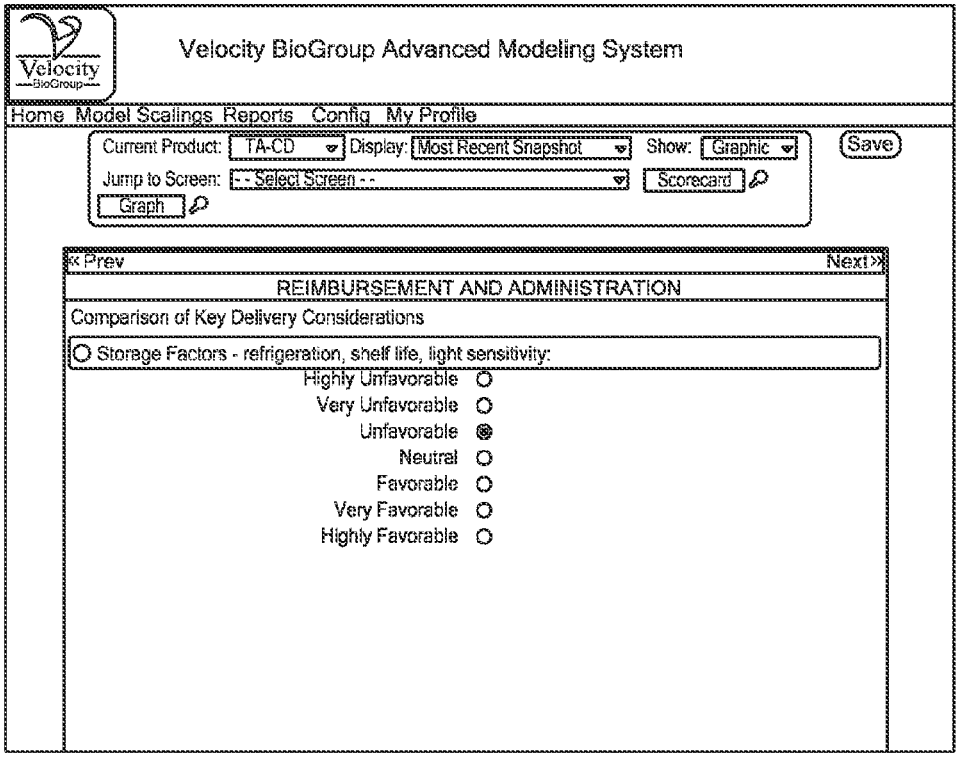

Refrigeration, shelf life, and light sensitivity are factors of concern in comparisons of most injectable versus oral preparations (FIG. 21). This explains why TA-CD (a vaccine) has an unfavorable rating in the measure.

Similarly, the measure of use surrounding the administration by needle versus oral, plus the viscosity of the compound (FIG. 22) which drives needle gauge (and therefore administration trauma!) adversely affects TA-CD versus SUBOXONE in the software prediction, but not against the other injectable comparator, VIVITROL, which requires an extremely large needle to administer a highly viscous solution.

Figure 23:
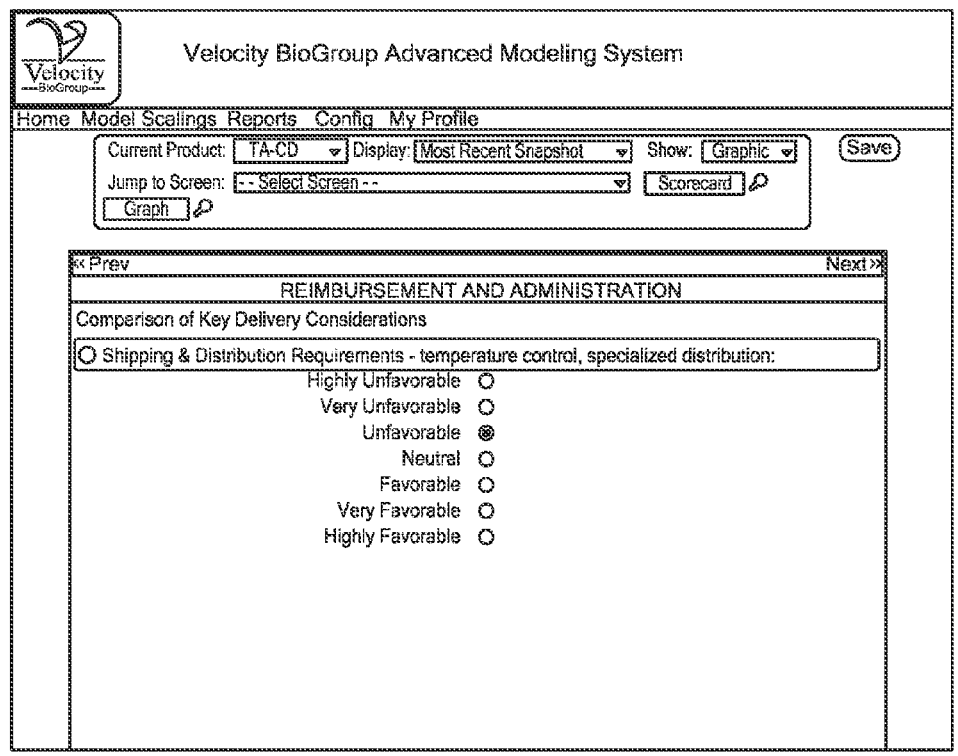

Temperature control during shipping and specialized distribution are important aspects of many injectable products, including vaccines (FIG. 23). These determine costs and complexity relative to oral medications and can increase the commercialization risks. Therefore, as in the case of the software example given here, the rating for TA-CD is unfavorable.

Figure 24:
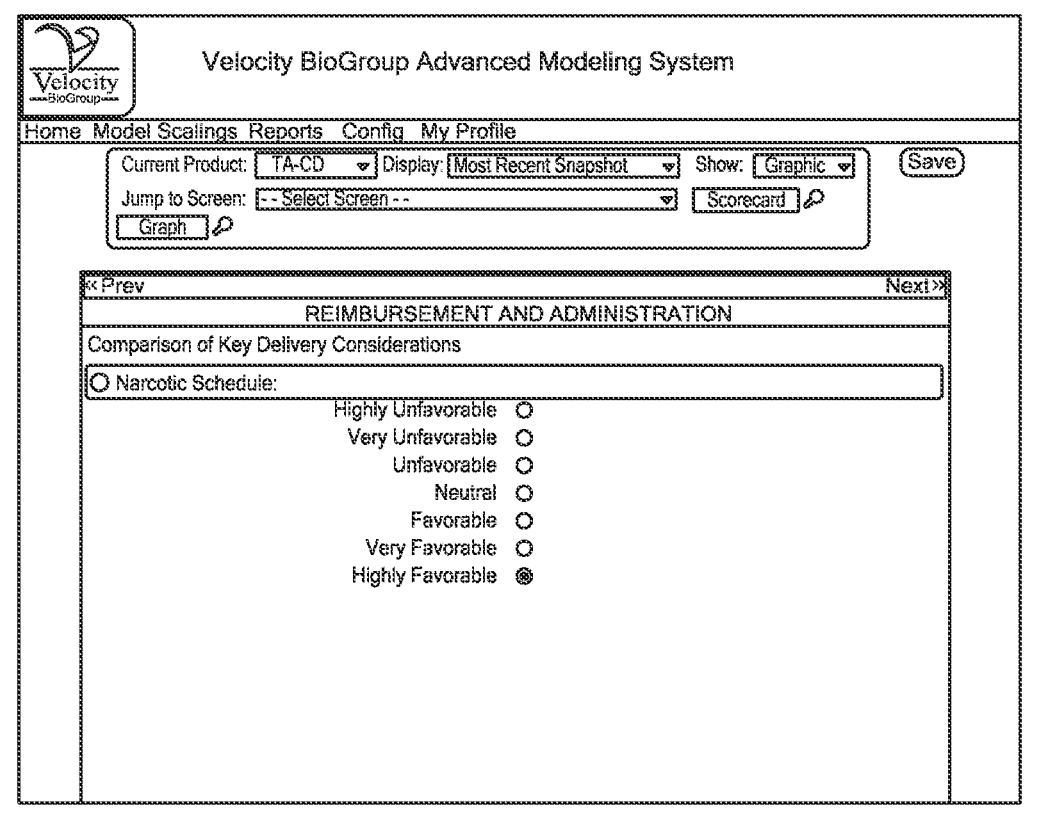

Finally, TA-CD will not require placement on the narcotic schedule, creating a highly favorable rating for this component (FIG. 24). This is important since narcotic scheduling impacts distribution, physician credentialing, and market use. SUBOXONE, one of the comparators, required significant marketplace preparation in order to overcome its status as a narcotic.

Key Government Market Drivers (FIGS. 25-28)

Predictors for marketplace access are based on the comparator products' access challenges in the same markets. Markets for access are chosen based on the 80/20 rule of looking to key customers who will impact the majority of the business.

Figure 25:
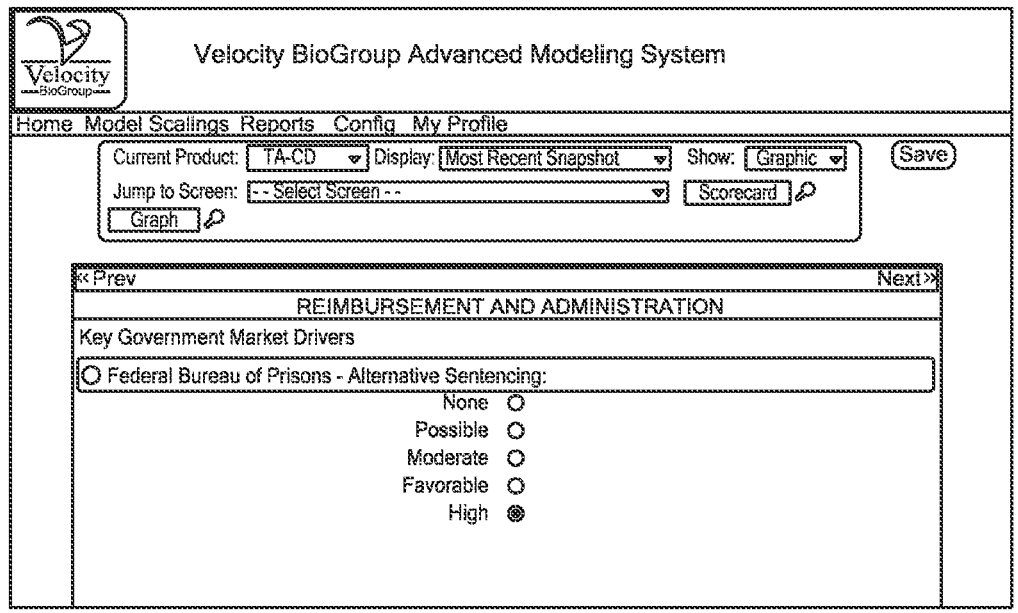

In the case of substance use disorder drugs, the core assumption driving the model is that the criminal justice system will be the primary access feeder for TA-CD use. Furthermore, trends towards both federal and state programs that offer treatment versus jail time (i.e., alternative sentencing) will be a significant predictor of the product's commercialization opportunities (FIG. 25).

Figure 26:
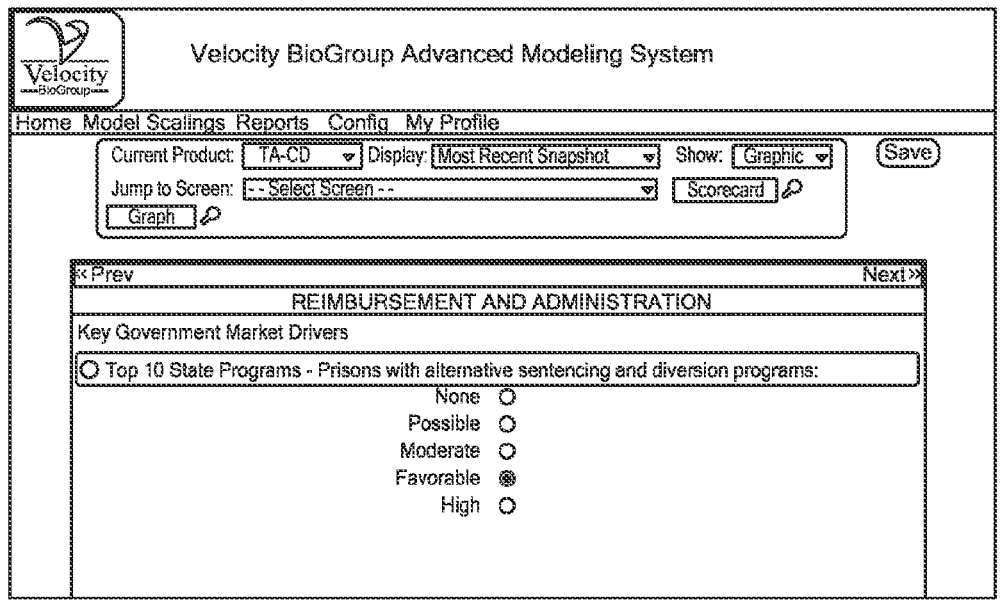

Since 80% of substance abuse treatment is paid through the government, public funding will be critical to the success of any new drug for this disorder. In this example, the top ten states (ranked by population size) are assessed based upon their use of alternative sentencing or diversion programs (FIG. 26). A favorable rating indicates a strong potential market for substance abuse therapies.

Figure 27:
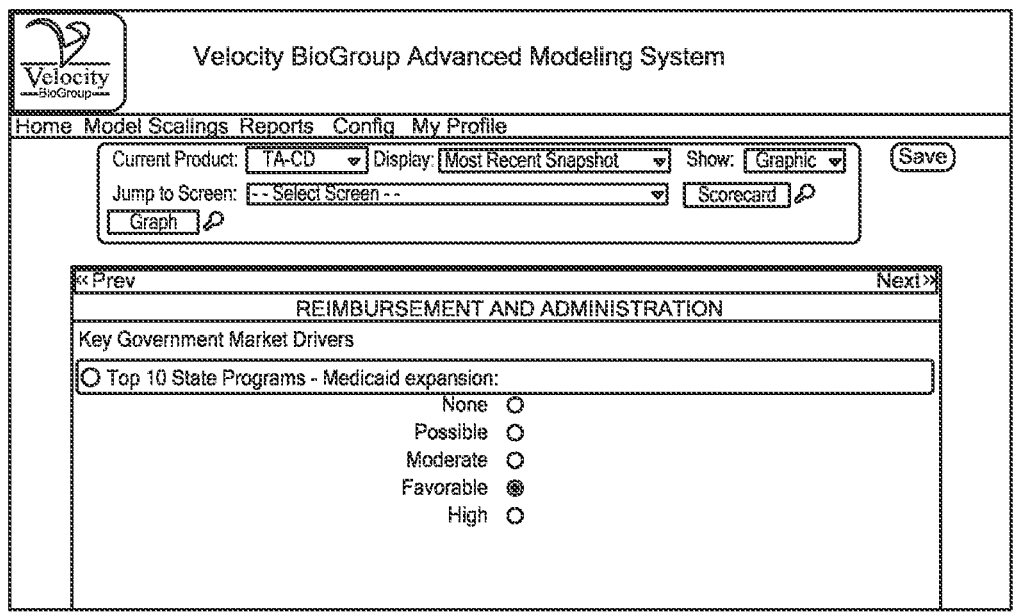

The third screen recognizes that Medicaid is the primary payer for these treatment services, and, in particular, recent changes in the law (e.g., the Patient Protection and Affordable Care Act of 2010) further support that expanded care for low income individuals will provide the funding to pay for these services (FIG. 27). The model captures the top ten programs in Medicaid (by population size) and measures the opportunity for TA-CD success in gaining access as favorable, given its specific profile and the needs of the payer.

Figure 28:
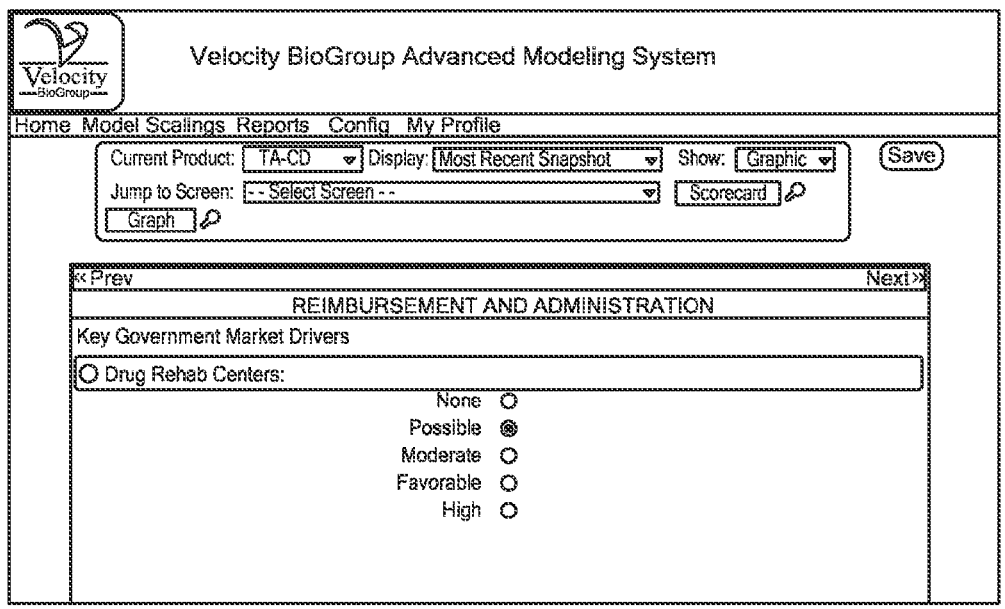

The last screen in the government market basket reflects one point of care delivery, that is, the drug rehabilitation centers (FIG. 28). In reality, these may also represent private sector payer access as well. Rehabilitation centers have more limited durations of stay than the vaccine primary series and booster programs demand (think of the number of shots required for children to get their vaccinations). Consequently, TA-CD has been rated as a "Possible" success within these institutions.

Figure 29:
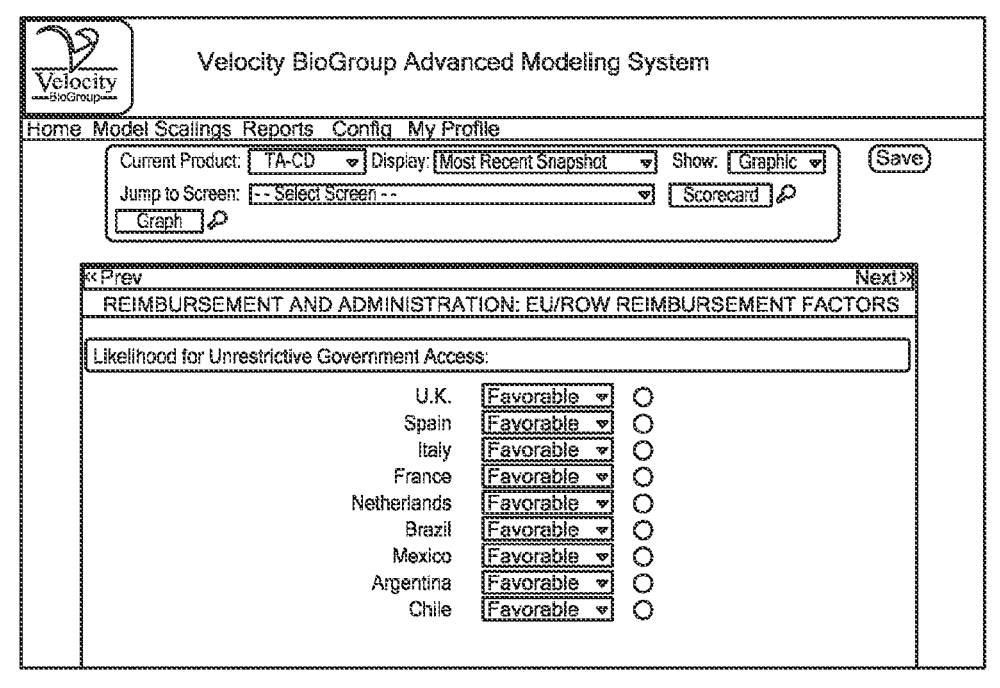

European (EU) & Rest of World (ROW) Access (FIG. 29)

The final screen in the model reflects predictions for specific global markets that can offer commercial viability for TA-CD. In this example, these non-US markets were selected with the epidemiological rates of incidence and prevalence of substance use disorder for cocaine use in mind. All of the selected markets were ranked "Favorable," reflecting the cost savings advantage of a vaccine versus daily intervention with an oral therapy. Given the extant cost-driven environment, however, making the case for new biologicals will be demanding, which is why the ranking was not "High." Each country selected had to pass certain criteria for both a "will to treat" and a "will to pay" in order to be ranked "Favorable" in terms of market access.

Part IV: Value Assessment

Figure 30:
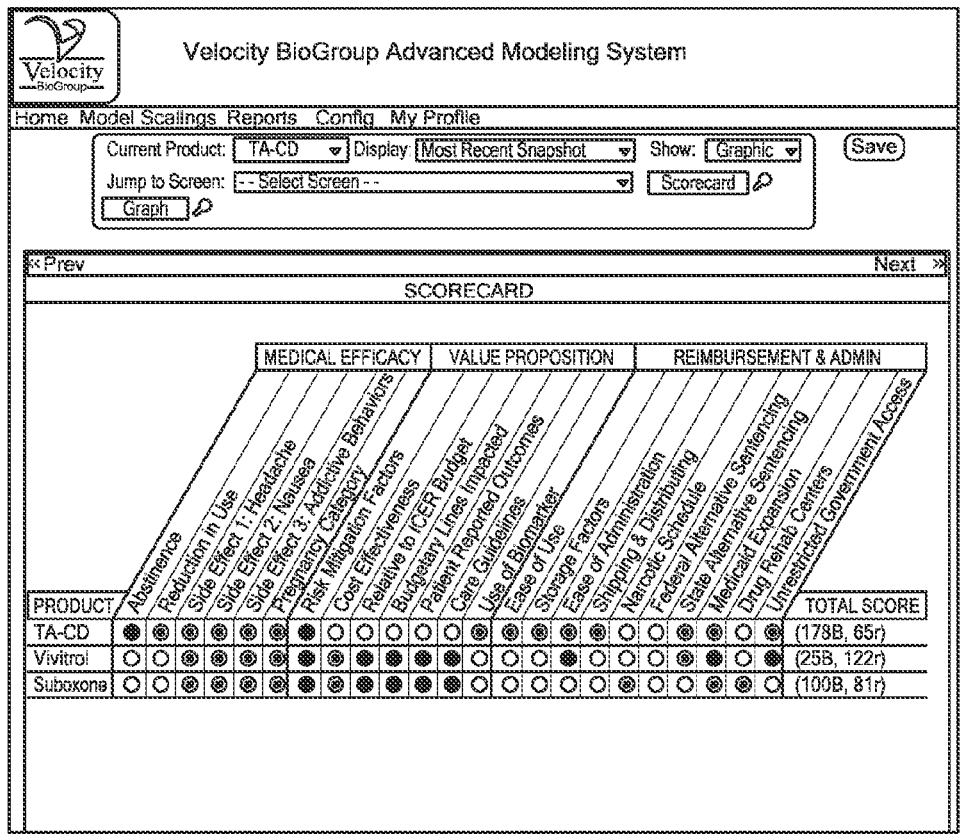
Figure 31:
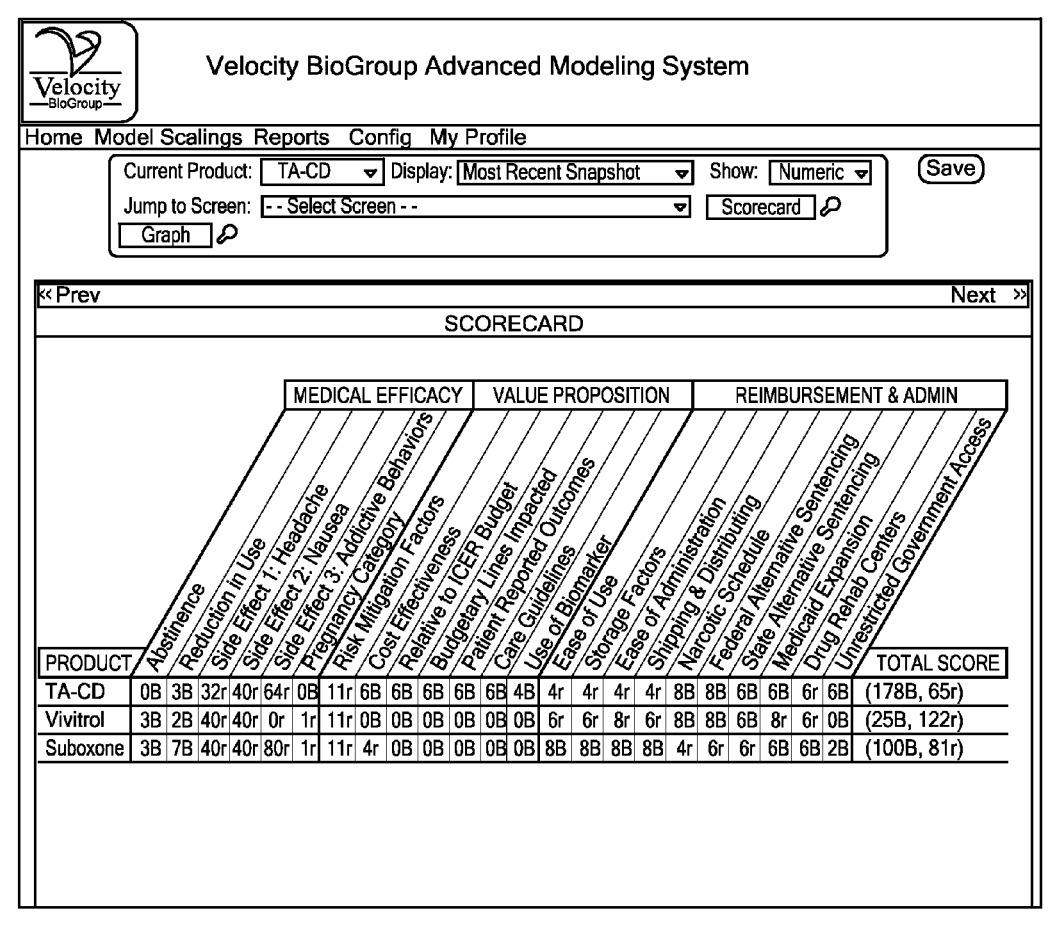

Scorecard (FIGS. 30-31)

As shown in FIG. 30, the scorecard is a compilation of data from the three categories outlined above: technology benefits/risks, value proposition, and market dynamics, with relative scaling factors applied. The scorecard provides a view of the final risk and benefit scores while displaying success and failure indicators for each of the three areas. Indicia, such as color and shape coding, can be used instead of, or in addition to, showing numeric scores. For example, colors can be coded from green, representing highly favorable outcomes, through red, depicting highly unfavorable outcomes for the therapy. Yellow and orange can represent the gradation between these extremes. Circles can represent the current scores. The scorecard represents a snapshot in time. As variables change in the model, such as the addition of new clinical trial data, the model instantaneously recalculates the risks and benefits. Changes in color depict changes to the data entered for the product.

The scorecard can also be viewed in a numeric format (as in FIG. 31), providing the user with the benefit and risk scores for each of the data points. The color coding follows the same practice described above. Changes between present and past scorecard ratings can be represented by both color and shape changes. For example, upward and downward arrows can represent an improvement or decline in results from the previous reporting period. A status quo measurement can be represented by circles instead of arrows and fully completed results for any metric can be represented by squares.

Figure 32:
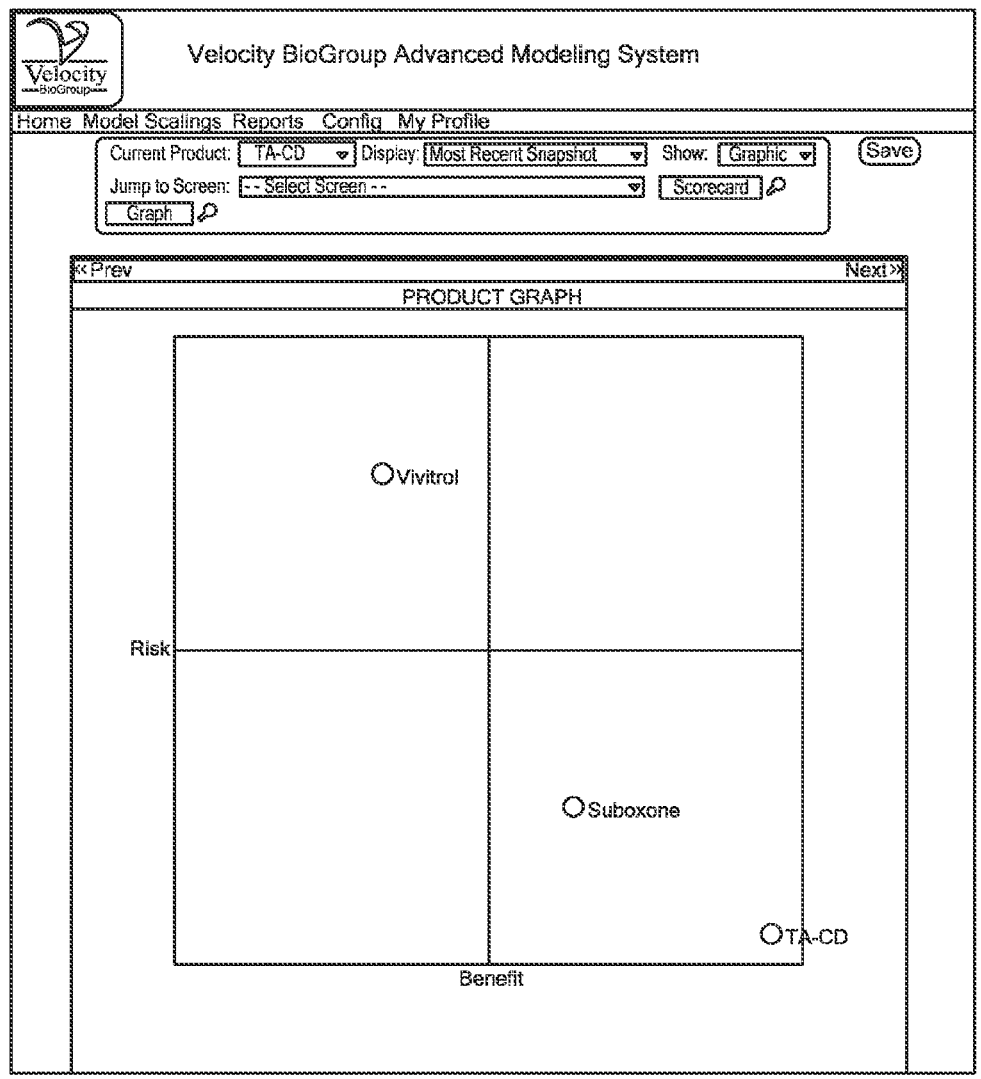

Product Graph (FIG. 32)

The final view of the product's value proposition is depicted on a graph along with the comparators. The y-axis represents the overall risk scores for the product. The x-axis represents the overall benefit scores. The ideal location for the product is in the bottom right quadrant of the graph, where benefit is high and risk is low. The graph shows the relative value proposition for each product and also provides guidance for product price points in the market. The graph is defined as an "X" and "Y" coordinate two-dimensional graph, located in Quadrant 1 of the Cartesian plane convention, which has four quadrants. Risk is considered a negative characteristic, usually placing it as the second coordinate of the convention (x, y) along the negative y-axis below the zero point. However, given the concern for "rising" or "intensifying" risk factors, and how analysts and reviewers typically refer to a "rising risk", using the y-axis above the zero point fits that idea. Therefore, although not technically accurate, we will use that commonly-referenced convention. Most government and business convention demands use of Quadrant 1 to explain ideas while referencing a graph/Cartesian coordinate using (x, y) coordinate graphs.

Market positioning on the graph is accomplished by setting an overlay of two lines in Quadrant 1 as detailed in the above screen shot. The midpoints are the average of the benefit scores of the existing market or proxy products for the x-axis and the average of the risk scores for the y-axis. The new market product's scores are not included in either of these average value calculations. The existing products are then positioned on the graph from their benefit scores as the x component and the risk scores as the y component. In addition, it will be observed that their positioning will also be relative to the average value lines of benefit and risk, either above or below, or to the right or left of these lines. This then sets the average values and outer boundaries of the market as it exists and how the marketed products therein are currently positioned for commercialization success.

Finally, the new market product x value is its Benefit score and its y value is derived from its risk score. These are then used to locate its position on quadrant 1, relative to A) the existing market products, B) the secondary lines, and C) the existing market product benefits and risks. This visual display provides added clarity for product pricing, development and justification of further investment for the product's research and development program.

Part V: Summary

A primary purpose of the evaluative tool described herein is to support the assessment of technologies during development in order to make critical decisions for an optimized development plan and for assessing the feasibility of continued investment. This software tool is the first to measure, weight, and integrate all of the critical factors that come into play in the development of a risk/benefit profile of a technology relative to its competitors, benchmarked around clinical trial measures, in order to determine its development and commercialization success.

The benefits of the software tool over existing technologies are many:

Provides for a consolidation of large amounts of data into a simplified scorecard for critical decision-making in medical innovation development, thus eliminating the need for unnecessary paperwork and uncontrolled and unmeasured processes;

Defines and distills the risk/benefit ratio of both medical innovation development and commercialization into easy-to-understand factors;

Allows for easy and early recognition of critical factors supporting or challenging innovation success;

Creates a comprehensive comparative effectiveness framework for evaluating new drug therapies for financing, development, acquisition or utilization;

Allows for a competitive analysis of drugs, biologics or devices in development relative to the current standard of care, or relative to those products that have proven the greatest marketplace or stakeholder acceptance.

Positions new assets in development for the most likely overall development and marketplace success, based on the track record of either competitors or market surrogates with the same market criteria, value proposition development and stakeholder community interests.

While this invention has been described in conjunction with the various exemplary embodiments outlined above, it is evident that many alternatives, modifications and variations will be apparent to those skilled in the art. Accordingly, the exemplary embodiments of the invention, as set forth above, are intended to be illustrative, not limiting. Various changes may be made without departing from the spirit and scope of the invention.

What is claimed is:

1. A computer-implemented method for evaluating a drug, biologic or medical device in research and development, the method comprising:
using a computerized processor for:
defining a maximum benefit numerical score representing total benefits of a drug, biologic or medical device based on clinical trial data;
defining a maximum risk numerical score representing total risks of the drug, biologic or medical device based on clinical trial data;
receiving identification of a plurality of model categories, wherein the model categories are selected from:
a plurality of medical efficacy and safety categories;
a plurality of value proposition categories; and
a plurality of market dynamics categories;
receiving scaled adjustment values associated with the identified model categories, wherein the scaled adjustment values represent importance of factor elements within a model category;
apportioning the maximum benefit numerical score among the identified model categories based on the scaled adjustment values associated with the model categories;
apportioning the maximum risk numerical score among the identified model categories based on the scaled adjustment values associated with the model categories;
receiving an identification of one or more factor elements defined within one or more of the model categories;
receiving a plurality of risk scores and benefit scores for the identified factor elements;
generating an overall numerical benefit score based on the aggregate of the benefit scores for the identified factor elements as adjusted by the scaled adjustment values associated with the model categories;
generating an overall numerical risk score based on the aggregate of the risk scores for the identified factor elements as adjusted by the scaled adjustment values associated with the model categories;
storing the overall numerical risk and overall numerical benefit scores for the drug, biologic or medical device as separate benefit and risk values in a computerized storage device; and
displaying the stored overall scores on one or more axes.

2. The method of claim 1, wherein a feasibility evaluation is reviewed by a convened panel of relevant category experts in terms of a range of qualitative values ranging from substantially disagree to substantially agree, and incorporating those results as part of the feasibility evaluation.

3. The method of claim 1, wherein the overall numerical risk and overall numerical benefit scores represent a feasibility of the drug, biologic or medical device to meet regulatory approval and achieve commercialization success.

4. The method of claim 1, wherein the adjustment values associated with the model categories comprise one or more multipliers.

5. The method of claim 1, further comprising creating a two-dimensional representation of the overall numerical risk and overall numerical benefit scores.

6. The method of claim 1, wherein the overall numerical risk and overall numerical benefit scores are predictive of commercialization success of the drug, biologic or medical device.

7. The method of claim 1, wherein the overall numerical risk score represents a market risk to a developer of the drug, biologic or medical device.

8. The method of claim 1, further comprising presenting a graphical comparative display of a plurality of drugs, biologics or medical devices in relation to each other in a two dimensional space, wherein a first dimension represents an overall numerical risk and a second dimension represents an overall numerical benefit of each of the drugs, biologics or medical devices.

9. The method of claim 1, further comprising receiving a qualitative descriptor representing quantitative clinical trial data for scoring benefit and risk.

10. The method of claim 9, wherein the qualitative descriptor is selected from a plurality of predefined effectiveness ratings for a drug, biologic or medical device under development.

11. The method of claim 1, wherein each of the model categories further comprises multiple factor elements.

12. The method of claim 1, wherein each of the model categories available for identification is dependent upon the drug, biologic or medical device, and the therapeutic area for which that drug, biologic or medical device is intended.

13. A computer-implemented method for evaluating a drug, biologic or medical device in research and development, the method comprising:
using a computerized processor for:
defining a maximum benefit numerical score representing total benefits of a drug, biologic or medical device based on clinical trial data;
defining a maximum risk numerical score representing total risks of the drug, biologic or medical device based on clinical trial data;
receiving identification of a plurality of model categories, wherein the model categories are selected from:
a plurality of medical efficacy and safety categories;
a plurality of value proposition categories; and
a plurality of market dynamics categories;
apportioning the maximum benefit numerical score among the identified model categories;
apportioning the maximum risk numerical score among the identified model categories;
receiving an identification of one or more factor elements defined within one or more of the model categories;
receiving a plurality of risk scores and benefit scores for the identified factor elements;
receiving scaled adjustment values associated with the identified factor elements, wherein the scaled adjustment values represent the importance of factor elements within a model category;
generating an overall numerical benefit score based on the aggregate of the benefit scores for the identified factor elements as adjusted by the scaled adjustment values associated with the identified factor elements;
generating an overall numerical risk score based on the aggregate of the risk scores for the identified factor elements as adjusted by the scaled adjustment values associated with the identified factor elements;
storing the overall numerical risk and overall numerical benefit scores for the drug, biologic or medical device as separate benefit and risk values in a computerized storage device; and
displaying the stored overall scores on one or more axes.

14. The method of claim 13, wherein a feasibility evaluation is reviewed by a convened panel of relevant category experts in terms of a range of qualitative values ranging from substantially disagree to substantially agree, and incorporating those results as part of the feasibility evaluation.

15. The method of claim 13, wherein the overall numerical risk and overall numerical benefit scores represent a feasibility of the drug, biologic or medical device to meet regulatory approval and achieve commercialization success.

16. The method of claim 13, further comprising presenting a graphical comparative display of a plurality of drugs, biologics or medical devices in relation to each other in a two dimensional space, wherein a first dimension represents an overall numerical risk and a second dimension represents an overall numerical benefit of each of the drugs, biologics or medical devices.

17. A computer system, comprising:
an input device;
an output device;
a processor configured for:
defining a maximum benefit numerical score representing total benefits of a drug, biologic or medical device based on clinical trial data;
defining a maximum risk numerical score representing total risks of the drug, biologic or medical device based on clinical trial data;
receiving identification of a plurality of model categories, wherein the model categories are selected from:
a plurality of medical efficacy and safety categories;
a plurality of value proposition categories; and
a plurality of market dynamics categories;
receiving scaled adjustment values associated with the identified model categories, wherein the scaled adjustment values represent importance of factor elements within a model category;
apportioning the maximum benefit numerical score among the identified model categories based on the scaled adjustment values associated with the model categories;
apportioning the maximum risk numerical score among the identified model categories based on the scaled adjustment values associated with the model categories;
receiving an identification of one or more factor elements defined within one or more of the model categories;
receiving a plurality of risk scores and benefit scores for the identified factor elements;
generating an overall numerical benefit score based on the aggregate of the benefit scores for the identified factor elements as adjusted by the scaled adjustment values associated with the model categories;
generating an overall numerical risk score based on the aggregate of the risk scores for the identified factor elements as adjusted by the scaled adjustment values associated with the model categories;
storing the overall numerical risk and overall numerical benefit scores for the drug, biologic or medical device as separate benefit and risk values in a computerized storage device; and
displaying the stored overall scores on one or more axes.

18. The system of claim 17, wherein the adjustment values associated with the model categories comprise one or more multipliers.

19. The system of claim 17, further comprising creating a two-dimensional representation of the overall numerical risk and overall numerical benefit scores.

20. The system of claim 17, wherein the overall numerical risk and overall numerical benefit scores are predictive of commercialization success of the drug, biologic or medical device.

* * * * *